US012780907B2

(12) United States Patent
Busfield

(10) Patent No.: US 12,780,907 B2
(45) Date of Patent: Nov. 3, 2026

(54) NGF-BINDING MOLECULES AND USES THEREOF

(71) Applicant: Scout Bio, Inc., Philadelphia, PA (US)

(72) Inventor: Samantha Busfield, Brunswick (AU)

(73) Assignee: Scout Bio, Inc., Philadelphia, PA (US)

( * ) Notice: Subject to any disclaimer, the term of this patent is extended or adjusted under 35 U.S.C. 154(b) by 1018 days.

(21) Appl. No.: 17/905,607

(22) PCT Filed: Mar. 3, 2021

(86) PCT No.: PCT/IB2021/051746
§ 371 (c)(1),
(2) Date: Sep. 2, 2022

(87) PCT Pub. No.: WO2021/176362
PCT Pub. Date: Sep. 10, 2021

(65) Prior Publication Data

US 2023/0110287 A1 Apr. 13, 2023

(30) Foreign Application Priority Data

Mar. 3, 2020 (AU) ................................ 2020900632

(51) Int. Cl.
*A61K 39/395* (2006.01)
*A61P 43/00* (2006.01)
*C07K 16/22* (2006.01)
*C12N 15/86* (2006.01)
*A61K 39/00* (2006.01)

(52) U.S. Cl.
CPC .............. *C07K 16/22* (2013.01); *A61P 43/00* (2018.01); *C12N 15/86* (2013.01); *A61K 2039/505* (2013.01); *C07K 2317/24* (2013.01); *C07K 2317/565* (2013.01)

(58) Field of Classification Search
None
See application file for complete search history.

(56) References Cited

U.S. PATENT DOCUMENTS

| | | | |
|---|---|---|---|
| 4,797,368 | A | 1/1989 | Carter et al. |
| 5,139,941 | A | 8/1992 | Muzyczka et al. |
| 5,478,745 | A | 12/1995 | Samulski et al. |
| 5,741,683 | A | 4/1998 | Zhou et al. |
| 5,892,019 | A | 4/1999 | Schlom et al. |
| 6,057,152 | A | 5/2000 | Samulski et al. |
| 6,204,059 | B1 | 3/2001 | Samulski et al. |
| 6,268,213 | B1 | 7/2001 | Samulski et al. |
| 6,342,390 | B1 | 1/2002 | Wiener et al. |
| 6,491,907 | B1 | 12/2002 | Rabinowitz et al. |
| 6,660,514 | B1 | 12/2003 | Zolotukhin et al. |
| 6,821,511 | B2 | 11/2004 | Kotin et al. |
| 6,951,753 | B2 | 10/2005 | Shenk et al. |
| 7,094,604 | B2 | 8/2006 | Snyder et al. |
| 7,172,893 | B2 | 2/2007 | Rabinowitz et al. |
| 7,201,898 | B2 | 4/2007 | Monahan et al. |
| 7,229,823 | B2 | 6/2007 | Samulski et al. |
| 7,282,199 | B2 | 10/2007 | Gao et al. |
| 7,439,065 | B2 | 10/2008 | Ferrari et al. |
| 7,588,772 | B2 | 9/2009 | Kay et al. |
| 7,790,449 | B2 | 9/2010 | Gao et al. |
| 7,906,111 | B2 | 3/2011 | Wilson et al. |
| 12,065,487 | B2 | 8/2024 | Busfield et al. |
| 2003/0042397 | A1 | 3/2003 | Tatsuki et al. |
| 2007/0036760 | A1 | 2/2007 | Wilson et al. |
| 2009/0197338 | A1 | 8/2009 | Vandenberghe et al. |
| 2018/0155415 | A1 | 6/2018 | Pavone |
| 2021/0221899 | A1 | 7/2021 | Steiniger et al. |
| 2023/0391862 | A1 | 12/2023 | Busfield et al. |
| 2025/0011412 | A1 | 1/2025 | Busfield et al. |

FOREIGN PATENT DOCUMENTS

| | | | |
|---|---|---|---|
| EP | 1310571 | A2 | 5/2003 |
| WO | WO-03042397 | A2 | 5/2003 |
| WO | WO-2005033321 | A2 | 4/2005 |
| WO | WO-2006110689 | A2 | 10/2006 |
| WO | WO-2006131951 | A2 | 12/2006 |
| WO | WO-2011126808 | A2 | 10/2011 |
| WO | WO-2012/153121 | | 11/2012 |

(Continued)

OTHER PUBLICATIONS

Aloe et al. Nerve Growth Factor: role in growth, differentiation and controlling cancer cell development. J. Exp. Clin. Can. Res. (2016) 35:116.*

Altschul, S.F. et al. "Basic Local Alignment Search Tool," Journal of Molecular Biology, Oct. 1990, 215(3):403-410.

Buning, H. et al., "Recent Developments in Adeno-associated Virus Vector Technology", J Gene Med, Jul. 2008; 10(7): 717-33.

Cattaneo, A., "Tanezumab, a recombinant humanized mAb against nerve growth factor for the treatment of acute and chronic pain", Curr Opin Mol Ther, Feb. 2010; 12(1): 94-106.

Chothia et al. "Canonical structures for the hypervariable regions of immunoglobulins" Journal of Molecular Biology (1987); 196(4):901-917.

Enomoto et al., "Anti-nerve growth factor monoclonal antibodies for the control of pain in dogs and cats", Veterinary Record 184(1):23, pp. 1-14 (2018).

(Continued)

*Primary Examiner* — Christine J Saoud
(74) *Attorney, Agent, or Firm* — COOLEY LLP

(57) ABSTRACT

Provided herein are antigen-binding molecules that specifically binds to nerve growth factor (NGF) and uses thereof. The antigen-binding molecules comprises an immunoglobulin heavy chain variable domain (VH) comprising a complementarity determining region 1 (VH CDR1) comprising the amino acid sequence of SEQ ID NO: 1, a VH CDR2 comprising the amino acid sequence of SEQ ID NO: 2 and a VH CDR3 comprising the amino acid sequence of SEQ ID NO: 3; and an immunoglobulin light chain variable domain (VL) comprising a complementarity determining region 1 (VL CDR1) comprising the amino acid sequence of SEQ ID NO: 4, a VL CDR2 comprising the amino acid sequence of SEQ ID NO: 5, and a VL CDR3 comprising the amino acid sequence of SEQ ID NO: 6.

13 Claims, 7 Drawing Sheets

Specification includes a Sequence Listing.

(56) References Cited

FOREIGN PATENT DOCUMENTS

| | | | |
|---|---|---|---|
| WO | WO-2012/153122 | | 11/2012 |
| WO | WO-2012/153126 | | 11/2012 |
| WO | WO-2012153123 | A1 | 11/2012 |
| WO | WO-2013/034900 | | 3/2013 |
| WO | WO-2013049493 | A1 | 4/2013 |
| WO | WO-2017040524 | A1 | 3/2017 |
| WO | WO-2021176362 | A1 | 9/2021 |
| WO | WO-2022087153 | A1 | 4/2022 |
| WO | WO-2022109403 | A1 | 5/2022 |
| WO | WO-2023034880 | A2 | 3/2023 |

OTHER PUBLICATIONS

Fisher, et al., "Transduction with recombinant adeno-associated virus for gene therapy is limited by leading-strand synthesis", Journal of Virology (1996); 70(1): 520-532.

Gribskov and Burgess, "Sigma factors from *E. coli*, B. subtilis, phage SP01, and phage T4 are homologous proteins", Nucleic Acids Res. Aug. 26, 1986; 14(16): 6745-63.

Grieger et al., "Adeno-associated virus as a gene therapy vector: vector development, production and clinical applications", Adv Biochem Eng Biotechnol, 2005; 99: 119-45.

Im et al., "The AAV origin binding protein Rep68 is an ATP-dependent site-specific endonuclease with DNA helicase activity", Cell, May 4, 1990; 61(3): 447-57.

Miyatake et al., "Transcriptional targeting of herpes simplex virus for cell-specific replication", J Virol, Jul. 1997; 71(7): 5124-32.

Pereira et al., "The adeno-associated virus (AAV) Rep protein acts as both a repressor and an activator to regulate AAV transcription during a productive infection", J Virol, Feb. 1997; 71(2): 1079-88.

Sandig et al., "HBV-derived promoters direct liver-specific expression of an adenovirally transduced LDL receptor gene", Gene Ther, Nov. 1996; 3(11): 1002-9.

Smith et al., "Comparison of biosequences". Advances in applied mathematics. Dec. 1, 1981;2(4):482-9.

Zhang et al., "Adenovirus-adeno-associated virus hybrid for large-scale recombinant adeno-associated virus production", Hum Gene Ther, Sep. 2009; 20(9): 922-9.

Zhang et al., "PKSolver: An add-in program for pharmacokinetic and pharmacodynamic data analysis in Microsoft Excel", Comput Methods Programs Biomed, Sep. 2010; 99(3): 306-14. Epub Feb. 21, 2010.

EP Application No. 21765118.1, Extended European Search Report Oct. 25, 2023, Applicant: Scout Bio, Inc., 7 pages.

EP Application No. 22865780.5, Extended European Search Report Oct. 16, 2025, Applicant Scout Bio, Inc.; 11 pages.

Gearing, D. P. et al., "A fully caninised anti-NGF monoclonal antibody for pain relief in dogs," BMC Veterinary Research. Nov. 9, 2013: 9: 226. doi: 10.1186/1746- 6148-9-226, 13 pages.

Gearing, D. P. et al., "In Vitro and In Vivo Characterization of a Fully Felinized Therapeutic Anti-Nerve Growth Factor Monoclonal Antibody for the Treatment of Pain in Cats," Journal of Veterinary Internal Medicine. Jul. 2016; 30(4): pp. 1129-1137. doi: 10.1111/jvim.13985. Epub Jun. 15, 2016.

PCT Application No. PCT/IB2021/051746, International Search Report and Written Opinion Apr. 30, 2021, Applicant: Scout Bio, Inc., 25 pages.

PCT Application No. PCT/IB2021/051746, International Preliminary Report on Patentability Sep. 6, 2022, Applicant: Scout Bio, Inc., 6 pages.

* cited by examiner

NGF-BINDING MOLECULES AND USES THEREOF

CROSS-REFERENCE TO RELATED APPLICATIONS

The present application is the U.S. National Stage of International Application No. PCT/IB2021/051746, filed Mar. 3, 2021, and claims priority to Australian Patent Application No. 2020900632, filed Mar. 3, 2020.

SEQUENCE LISTING

The present application contains a Sequence Listing which is being submitted electronically in TXT file format and is hereby incorporated by reference in its entirety. Said TXT copy is named 35556993_ST25_txt, was created on Mar. 3, 2020, and is 40,882 bytes in size.

FIELD OF INVENTION

The invention relates generally to antigen-binding molecules. In particular, the invention relates to antigen-binding molecules that specifically bind to and neutralise the activity of nerve growth factor (NGF) and uses thereof for the treatment of conditions associated with abnormal NGF expression and/or activity, such as pain.

BACKGROUND

All references, including any patent or patent application cited in this specification are hereby incorporated by reference to enable full understanding of the invention. Nevertheless, such references are not to be read as constituting an admission that any of these documents forms part of the common general knowledge in the art, in Australia or in any other country.

Pain, including chronic pain, can be a debilitating condition with far reaching social and economic consequences. Whilst a plethora of analgesic compounds have been prescribed for the treatment or prevention of pain in both humans and non-human animals, examples of which include local and general anaesthetics, opioid analgesics, α2 agonists, non-steroidal anti-inflammatory drugs (NSAIDs) and steroids, their efficacy can vary. Moreover, current analgesics typically require frequent administration over extended periods of time, which contributes, at least in part, to some of the adverse side effects associated with the long term use, including addiction and reduced efficacy.

As noted by Enomoto et al. (2019, *Veterinary Record;* 184(1):23), current pharmacological treatment of pain largely centres around non-steroidal anti-inflammatory drugs (NSAIDs) to relieve pain and promote functional improvement. Globally, several NSAIDs are approved for use in dogs, but only two NSAIDs are approved for use long-term in cats and only in certain countries. Despite their widespread use and obvious benefit in many cases, NSAIDs are not always sufficiently effective when used as monotherapy. Additionally, Enomoto et al. note there are safety and tolerability concerns with their use in both dogs and cats. Beyond cyclooxygenase-inhibiting NSAIDs and the recently approved piprant NSAID, a prostaglandin receptor antagonist, grapiprant, treatment options for the control of pain are very limited. Evidence for efficacy of so-called adjunctive analgesics is also limited. While the authors noted there are few proven non-drug therapies and none has been shown to provide rapid pain relief. This includes pain associated with inflammatory conditions such as osteoarthritis, which remains a challenging clinical entity to treat and is one of the most common reasons for euthanasia in dogs. Therefore, there remains an urgent need for improved analgesics that are effective for both human and veterinary applications, yet also avoid or at least partly alleviate some of the aforementioned problems associated with existing analgesics.

Nerve growth factor (NGF) is a secreted polypeptide and member of the neurotrophin family that is involved in a number of different signalling pathways. For example, NGF has been shown to promote the survival and differentiation of sensory and sympathetic neurons via two membrane bound receptors—p75, a low affinity NGF receptor, and TrkA, a transmembrane tyrosine kinase and a high affinity NGF receptor. The binding of NGF to TrkA or p75 results in an upregulation of neuropeptides in sensory neurons, which typically results in pain perception, or nociception.

NGF antagonists have been used to treat pain and pain sensitivity in humans, dogs and cats. For example, Cattaneo (2010*, Curr. Op. Mol. Ther.* 12(1):94-106) and WO 2006/131951 both describe the use of a humanised form of the rat alphaD11 (αD11) monoclonal antibody, which retains binding specificity to mouse NGF, but also binds to the human and rat forms of NGF. The primary rationale for humanising a donor antibody such as the rat αD11 monoclonal antibody is to minimise the production of neutralising antibodies that would otherwise result from a human anti-rat antibody response against rodent-derived antibodies following administration to a human subject in the course of, for example, antibody therapy. In Cattaneo (2010) and WO 2006/131951, the CDR regions of the rat-derived αD11 monoclonal antibody were grafted onto the framework regions derived from human immunoglobulin sequences, where the human framework sequences were selected for closest sequence identity to the corresponding framework regions of the rat αD11 antibody. Whilst CDR grafting removes FR sequences that would otherwise be foreign to and raise an immune response against the immunoglobulin, it is frequently associated with a loss of binding specificity and selectivity to the target antigen. The loss of binding specificity and selectivity is typically remedied by back-mutating one or more amino acid residues across the target species-derived FR sequences; that is, by replacing one or more amino acid residues across the modified framework regions of the target species with the corresponding residue from the same position in the framework region(s) of the donor antibody. However, whilst this can rescue binding specificity and selectivity, the introduction of amino acid residues from the donor antibody likely introduces an amino acid residue that would be foreign to the target species; that is, to the species to which the modified antibody is to be administered. The method described in WO 2012/153121 seeks to overcome the problem of back-mutating by comparing the amino acid residues across the framework regions of a donor anti-NGF antibody (such as the rat-derived αD11 monoclonal antibody) to the corresponding framework region sequences of one or more antibodies from a target species (e.g., canine) and substituting only those residues across the framework regions that are identified as being foreign at a corresponding position having regard to the framework regions from the target species, such that the modified antibody no longer contains any amino acid residue in its framework regions that would be foreign to the target species. This advantageously minimises the number of amino acid substitutions required and avoids the need for back-mutations that would otherwise be required to preserve binding specificity and selectivity of the modified donor antibody.

Whilst advances have been made in the design of anti-NGF antibodies for therapeutic use, including for the treatment and prevention of pain, it is to be noted that none has yet been approved for use in humans (Enomoto et al, 2019; supra) and only limited data are available for veterinary use. Thus, there is still an urgent need for improved NGF binding molecules that can be used in therapy, including for the treatment and prevention of pain in human and non-human animals such as dogs, cats and horses, which overcome or at least partly alleviate one or more of the above-mentioned difficulties associated with existing treatment modalities.

SUMMARY

The present disclosure is predicated, at least in part, on an improved anti-NGF binding molecule comprising complementarity determining regions (CDR) that are capable of binding specifically to native NGF of both human and non-human species (e.g., canine and feline) and whose framework regions can be modified for compatibility with a target species without loss of binding specificity and selectivity to native NGF. The NGF-binding molecules disclosed herein are therefore amenable to use in the treatment and prevention of conditions associated with abnormal NGF levels and/or activity, including pain and arthritis. The present disclosure is also predicated, at least in part, on the inventor's surprising finding that a single amino acid modification to the second residue of the heavy chain variable region CDR1 sequence of the rat-derived αD11 antibody (as previously described in WO 2006/131951) enhances expression of the recombinant antigen-binding molecule.

Thus, in an aspect disclosed herein, there is provided an antigen-binding molecule that specifically binds to nerve growth factor (NGF), wherein the antigen-binding molecule comprises an immunoglobulin heavy chain variable domain (VH) and an immunoglobulin light chain variable domain (VL), wherein the VH comprises a complementarity determining region 1 (VH CDR1) comprising the amino acid sequence of SEQ ID NO: 1, a VH CDR2 comprising the amino acid sequence of SEQ ID NO: 2 and a VH CDR3 comprising the amino acid sequence of SEQ ID NO: 3; and wherein the VL comprises a complementarity determining region 1 (VL CDR1) comprising the amino acid sequence of SEQ ID NO: 4, a VL CDR2 comprising the amino acid sequence of SEQ ID NO: 5, and a VL CDR3 comprising the amino acid sequence of SEQ ID NO: 6:

VH CDR1

(SEQ ID NO: 1)

GLSLTNNNVN

VH CDR2

(SEQ ID NO: 2)

GVWAGGATDYNSA-$X_1$-KS

VH CDR3

(SEQ ID NO: 3)

DGGYSSSTLYAM-$X_2$-$X_3$

VL CDR1

(SEQ ID NO: 4)

RASEDIYNALA

VL CDR2

(SEQ ID NO: 5)

-continued

NTDTLHT

VL CDR3

(SEQ ID NO: 6)

QHYFHYPRT wherein $X_1$ is leucine or a conservative amino acid substitution thereof;

wherein $X_2$ is aspartic acid or a conservative amino acid substitution thereof; and wherein $X_3$ is alanine or a conservative amino acid substitution thereof.

In an embodiment:

$X_1$ is leucine or valine;

$X_2$ is aspartic acid or glutamic acid; and $X_3$ is alanine or valine.

In an embodiment:

$X_1$ is valine;

$X_2$ is aspartic acid; and $X_3$ is alanine.

In an embodiment:

$X_1$ is valine;

$X_2$ is glutamic acid; and $X_3$ is alanine.

In an embodiment:

$X_1$ is valine;

$X_2$ is glutamic acid; and $X_3$ is valine.

In an embodiment:

$X_1$ is valine;

$X_2$ is aspartic acid; and $X_3$ is valine.

In an embodiment:

$X_1$ is leucine;

$X_2$ is aspartic acid; and $X_3$ is valine.

In an embodiment:

$X_1$ is leucine;

$X_2$ is glutamic acid; and $X_3$ is valine.

In an embodiment:

$X_1$ is leucine;

$X_2$ is glutamic acid; and $X_3$ is alanine.

In an embodiment:

$X_1$ is leucine;

$X_2$ is aspartic acid; and $X_3$ is alanine.

In an embodiment, the antigen-binding molecule comprises:

(a) a VH framework region 1 (FR1) comprising an amino acid sequence having at least 80% sequence identity to an amino acid sequence selected from the group consisting of SEQ ID NO: 16, 20, 24, 28 and 32;

(b) a VH FR2 comprising an amino acid sequence having at least 80% sequence identity to an amino acid sequence selected from the group consisting of SEQ ID NO: 17, 21, 25, 29 and 33;

(c) a VH FR3 comprising an amino acid sequence having at least 80% sequence identity to an amino acid sequence selected from the group consisting of SEQ ID NO: 18, 22, 25, 30 and 34;

(d) a VH FR4 comprising an amino acid sequence having at least 80% sequence identity to an amino acid sequence selected from the group consisting of SEQ ID NO: 19, 23, 26, 31 and 35;

(e) a VL FR1 comprising an amino acid sequence having at least 80% sequence identity to an amino acid sequence selected from the group consisting of SEQ ID NO: 36, 40, 44 and 48;

(f) a VL FR2 comprising an amino acid sequence having at least 80% sequence identity to an amino acid sequence selected from the group consisting of SEQ ID NO, 37, 41, 45 and 49;

(g) a VL FR3 comprising an amino acid sequence having at least 80% sequence identity to an amino acid sequence selected from the group consisting of SEQ ID NO: 38, 42, 46 and 50; and (h) a VL FR4 comprising an amino acid sequence having at least 80% sequence identity to an amino acid sequence selected from the group consisting of SEQ ID NO: 39, 43, 47 and 51.

In another embodiment, (a) the VH comprises an amino acid sequence having at least 80% sequence identity to an amino acid sequence selected from the group consisting of SEQ ID NO: 7, SEQ ID NO: 8, SEQ ID NO: 9, SEQ ID NO: 10 and SEQ ID NO: 11, and (b) the VL comprises an amino acid sequence having at least 80% sequence identity to an amino acid sequence selected from the group consisting of SEQ ID NO: 12, SEQ ID NO; 13, SEQ ID NO: 14 and SEQ ID NO: 15.

In yet another embodiment, the antigen-binding molecule comprises:

(a) a VH FR1 comprising an amino acid sequence having at least 80% sequence identity to a VHFR1 amino acid sequence of SEQ ID NO: 54, (b) a VH FR2 comprising an amino acid sequence having at least 80% sequence identity to a VHFR2 amino acid of SEQ ID NO: 55, (c) a VH FR3 comprising an amino acid sequence having at least 80% sequence identity to a VHFR3 amino acid sequence of SEQ ID NO: 56, (d) a VH FR4 comprising an amino acid sequence having at least 80% sequence identity to a VHFR4 amino acid sequence of SEQ ID NO: 57, (e) a VL FR1 comprising an amino acid sequence having at least 80% sequence identity to a VLFR1 amino acid sequence of SEQ ID NO:58, (f) a VL FR2 comprising an amino acid sequence having at least 80% sequence identity to a VLFR2 amino acid sequence of SEQ ID NO:59, (g) a VL FR3 comprising an amino acid sequence having at least 80% sequence identity to a VLFR3 amino acid sequence of SEQ ID NO: 60, and (h) a VL FR4 comprising an amino acid sequence having at least 80% sequence identity to a VHFR4 amino acid sequence of SEQ ID NO: 61.

In another embodiment, the antigen-binding molecule comprises:

(a) the VH comprises an amino acid sequence having at least 80% sequence identity to a VH amino acid sequence of SEQ ID NO: 52, and (b) the VL comprises an amino acid sequence having at least 80% sequence identity to a VL amino acid sequence of SEQ ID NO: 53.

In an embodiment, the antigen-binding molecule is an antibody or an NGF-binding fragment thereof. Suitable NGF-binding fragments will be familiar to persons skilled in the art, illustrative examples of which include an Fab fragment, an scFab, an Fab', a single chain variable fragment (scFv) and a one-armed antibody. Thus, in an embodiment disclosed herein, the NGF-binding fragment is selected from the group consisting of an Fab fragment, an scFab, an Fab', a single chain variable fragment (scFv) and a one-armed antibody.

In an embodiment, the antigen-binding molecule is a humanized, a caninized, a felinized or an equinized antibody or an NGF-binding fragment thereof.

In another aspect disclosed herein, there is provided an isolated nucleic acid molecule comprising a nucleic acid sequence encoding the antigen-binding molecule as described herein.

Also disclosed herein is an expression construct comprising a nucleic acid sequence encoding the antigen-binding molecule described herein, wherein the nucleic acid sequence is operably linked to one or more regulatory sequences.

The present disclosure also extends to a host cell comprising the expression construct described herein.

The present disclosure also extends to vector comprising a nucleic acid sequence encoding the antigen-binding molecule described herein. Suitable vectors will be familiar to persons skilled in the art. In an embodiment, the vector is an AAV vector.

The present disclosure also extends to a pharmaceutical composition comprising the antigen-binding molecule described herein, and a pharmaceutically acceptable carrier.

In another aspect disclosed herein, there is provided a method of treating or preventing a condition associated with increased expression and/or increased activity of NGF, the method comprising administering to a subject in need thereof the antigen-binding molecule, the vector, or the pharmaceutical composition, as herein described.

Conditions associated with increased expression and/or increased activity of NGF will be familiar to persons skilled in the art, illustrative examples of which include pain, arthritis and cancer.

Illustrative examples of pain associated with increased expression and/or increased activity of NGF include neuropathic, inflammatory, pruritic, peri-operative, post-operative and post-surgical pain.

Illustrative examples of arthritis associated with increased expression and/or increased activity of NGF include immune mediated polyarthritis, rheumatoid arthritis and osteoarthritis.

In another aspect disclosed herein, there is provided a method of treating or preventing a tumour induced to proliferate by NGF and conditions associated therewith, the method comprising administering to a subject in need thereof the antigen-binding molecule, the vector, or the pharmaceutical composition, as herein described. An illustrative example of a tumour induced to proliferate by NGF and conditions associated therewith is osteosarcoma.

Also disclosed herein is a kit comprising the antigen-binding molecule, the vector, or the pharmaceutical composition, as herein described.

The present disclosure also extends to use of the antigen-binding molecule, or the vector, as herein described, in the manufacture of a medicament for treating or preventing a condition associated with increased expression and/or increased activity of NGF in a subject in need thereof.

The present disclosure also extends to use of the antigen-binding molecule, or the vector, as herein described, in the manufacture of a medicament for treating or preventing a tumour induced to proliferate by NGF and conditions associated therewith in a subject in need thereof.

The present disclosure also extends to the antigen-binding molecule, the vector, or the pharmaceutical composition, as herein described, for use in the treatment or prevention of a condition associated with increased expression and/or increased activity of NGF in a subject in need thereof.

The present disclosure also extends to the antigen-binding molecule, the vector, or the pharmaceutical composition, as herein described, for use in the treatment or prevention of a tumour induced to proliferate by NGF and conditions associated therewith in a subject in need thereof.

BRIEF DESCRIPTION OF DRAWINGS

Embodiments of the present invention are hereafter described, by way of non-limiting example only, with reference to the accompanying drawings in which.

DETAILED DESCRIPTION

Figure 1:
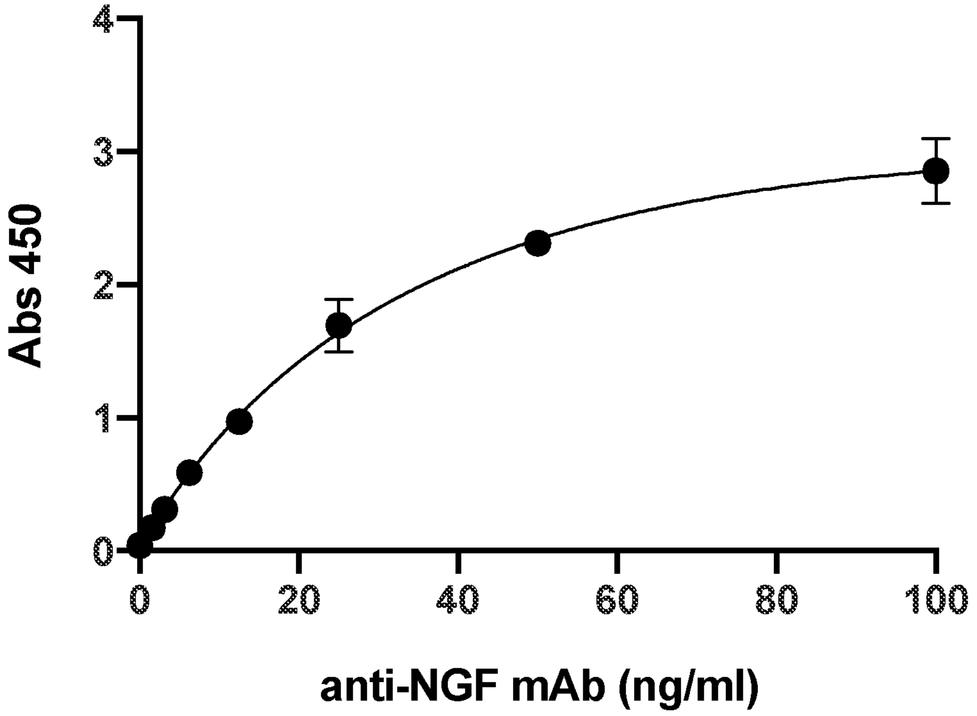
FIG. 1 shows binding of the feline/felinized anti-NGF antibody (Fe1) to murine NGF, as determined by enzyme-linked immunosorbent assay (ELISA). The data shown are mean±/−SD.

As described elsewhere herein, the present disclosure is predicated, at least in part, on an improved anti-NGF binding molecule comprising complementarity determining regions (CDRs) that are capable of binding specifically to native NGF of both human and non-human species (e.g., canine and feline) and whose framework regions can be modified for compatibility with a target species without loss of binding specificity and selectivity to native NGF. The present disclosure is also predicated, at least in part, on the inventor's surprising finding that a single amino acid modification to the second residue of the heavy chain variable region CDR1 sequence of the rat-derived αD11 antibody (as previously described in WO 2006/131951) enhances the expression of the recombinant antigen-binding molecule.

Thus, disclosed herein is an antigen-binding molecule that is capable of binding specifically to nerve growth factor (NGF), wherein the antigen-binding molecule comprises an immunoglobulin heavy chain variable domain (VH) and an immunoglobulin light chain variable domain (VL), wherein the VH comprises a complementarity determining region 1 (VH CDR1) comprising the amino acid sequence of SEQ ID NO: 1, a VH CDR2 comprising the amino acid sequence of SEQ ID NO: 2 and a VH CDR3 comprising the amino acid sequence of SEQ ID NO: 3; and wherein the VL comprises a complementarity determining region 1 (VL CDR1) comprising the amino acid sequence of SEQ ID NO: 4, a VL CDR2 comprising the amino acid sequence of SEQ ID NO: 5, and a VL CDR3 comprising the amino acid sequence of SEQ ID NO: 6:

VH CDR1
(SEQ ID NO: 1)
GLSLTNNNVN

VH CDR2
(SEQ ID NO: 2)
GVWAGGATDYNSA-$X_1$-KS

VH CDR3
(SEQ ID NO: 3)
DGGYSSSTLYAM-$X_2$-$X_3$

VL CDR1
(SEQ ID NO: 4)
RASEDIYNALA

VL CDR2
(SEQ ID NO: 5)
NTDTLHT

VL CDR3
(SEQ ID NO: 6)
QHYFHYPRT wherein $X_1$ is leucine or a conservative amino acid substitution thereof;

wherein $X_2$ is aspartic acid or a conservative amino acid substitution thereof; and wherein $X_3$ is alanine or a conservative amino acid substitution thereof.

A "conservative amino acid substitution" is to be understood as meaning a substitution in which the amino acid residue is replaced with an amino acid residue having a similar side chain. Families of amino acid residues having similar side chains have been defined in the art, which can be generally sub-classified as shown in the table "Amino Acid Classification", below:

AMINO ACID SUB-CLASSIFICATION

| Sub-classes | Amino acids |
|---|---|
| Acidic | Aspartic acid, Glutamic acid |
| Basic | Noncyclic: Arginine, Lysine; Cyclic: Histidine |
| Charged | Aspartic acid, Glutamic acid, Arginine, Lysine, Histidine |
| Small | Glycine, Serine, Alanine, Threonine, Proline |
| Polar/neutral | Asparagine, Histidine, Glutamine, Cysteine, Serine, Threonine |

-continued

| AMINO ACID SUB-CLASSIFICATION | |
|---|---|
| Sub-classes | Amino acids |
| Polar/large | Asparagine, Glutamine |
| Hydrophobic | Tyrosine, Valine, Isoleucine, Leucine, Methionine, Phenylalanine, Tryptophan |
| Aromatic | Tryptophan, Tyrosine, Phenylalanine |
| Residues that influence chain orientation | Glycine and Proline |

Conservative amino acid substitution also includes groupings based on side chains. For example, a group of amino acids having aliphatic side chains is glycine, alanine, valine, leucine, and isoleucine; a group of amino acids having aliphatic-hydroxyl side chains is serine and threonine; a group of amino acids having amide-containing side chains is asparagine and glutamine; a group of amino acids having aromatic side chains is phenylalanine, tyrosine, and tryptophan; a group of amino acids having basic side chains is lysine, arginine, and histidine; and a group of amino acids having sulfur-containing side chains is cysteine and methionine. For example, it is reasonable to expect that replacement of a leucine with an isoleucine or valine, an aspartate with a glutamate, a threonine with a serine, or a similar replacement of an amino acid with a structurally related amino acid will not have a major effect on the properties of the resulting variant polypeptide. Whether an amino acid change results in a functional polypeptide can readily be determined by assaying its activity.

Conservative substitutions are also shown in the table below (EXEMPLARY AND PREFERRED AMINO ACID SUBSTITUTIONS). Amino acid substitutions falling within the scope of the invention, are, in general, accomplished by selecting substitutions that do not differ significantly in their effect on maintaining (a) the structure of the peptide backbone in the area of the substitution, (b) the charge or hydrophobicity of the molecule at the target site, or (c) the bulk of the side chain. After the substitutions are introduced, the variants can be screened for their ability to bind specifically to NGF using methods known to persons skilled in the art, including those methods described elsewhere herein.

| EXEMPLARY AND PREFERRED AMINO ACID SUBSTITUTIONS | | |
|---|---|---|
| Original Residue | Exemplary Substitutions | Preferred Substitutions |
| Ala | Val, Leu, Ile | Val |
| Arg | Lys, Gln, Asn | Lys |
| Asn | Gln, His, Lys, Arg | Gln |
| Asp | Glu | Glu |
| Cys | Ser | Ser |
| Gln | Asn, His, Lys, | Asn |
| Glu | Asp, Lys | Asp |
| Gly | Pro | Pro |
| His | Asn, Gln, Lys, Arg | Arg |
| Ile | Leu, Val, Met, Ala, Phe, Norleu | Leu |
| Leu | Norleu, Ile, Val, Met, Ala, Phe | Ile |
| Lys | Arg, Gln, Asn | Arg |
| Met | Leu, Ile, Phe | Leu |
| Phe | Leu, Val, Ile, Ala | Leu |
| Pro | Gly | Gly |
| Ser | Thr | Thr |
| Thr | Ser | Ser |

-continued

| EXEMPLARY AND PREFERRED AMINO ACID SUBSTITUTIONS | | |
|---|---|---|
| Original Residue | Exemplary Substitutions | Preferred Substitutions |
| Trp | Tyr | Tyr |
| Tyr | Trp, Phe, Thr, Ser | Phe |
| Val | Ile, Leu, Met, Phe, Ala, Norleu | Leu |

In an embodiment, $X_1$ is leucine or valine, $X_2$ is aspartic acid or glutamic acid and $X_3$ is alanine or valine. In an embodiment, $X_1$ is leucine. In an embodiment, $X_1$ is valine. In an embodiment, $X_2$ is aspartic acid. In an embodiment, $X_2$ is glutamic acid. In an embodiment, $X_3$ is alanine. In an embodiment, $X_3$ is valine.

In an embodiment:

$X_1$ is leucine or valine;

$X_2$ is aspartic acid or glutamic acid; and $X_3$ is alanine or valine.

In an embodiment:

$X_1$ is valine;

$X_2$ is aspartic acid; and $X_3$ is alanine.

In an embodiment:

$X_1$ is valine;

$X_2$ is glutamic acid; and $X_3$ is alanine.

In an embodiment:

$X_1$ is valine;

$X_2$ is glutamic acid; and $X_3$ is valine.

In an embodiment:

$X_1$ is valine;

$X_2$ is aspartic acid; and $X_3$ is valine.

In an embodiment:

$X_1$ is leucine;

$X_2$ is aspartic acid; and $X_3$ is valine.

In an embodiment:

$X_1$ is leucine;

$X_2$ is glutamic acid; and $X_3$ is valine.

In an embodiment:

$X_1$ is leucine;

$X_2$ is glutamic acid; and $X_3$ is alanine.

In an embodiment:

$X_1$ is leucine;

$X_2$ is aspartic acid; and $X_3$ is alanine.

By "antigen-binding molecule" is meant a molecule that has binding affinity for a target antigen. It will be understood that this term extends to immunoglobulins, immunoglobulin fragments and non-immunoglobulin-derived protein frameworks that exhibit antigen-binding activity. Illustrative examples of suitable antigen-binding molecules include antibodies and antigen-binding fragments thereof. Preferably, the antigen-binding molecule binds specifically to NGF so as to neutralise, or substantially neutralise, its activity. The term "neutralise" is understood to mean that the antigen-binding molecule will bind to NGF and inhibit, reduce, abrogate, block or otherwise prevent the ability of the NGF molecule to bind to its native receptor (e.g., p75 or TrkA). In some embodiments, the antigen-binding molecule will completely neutralise the activity of NGF (in vivo or in vitro) such that there is no or negligible NGF activity when compared to the absence of the antigen-binding molecule. In other embodiments, the antigen-binding molecule will partially neutralise the activity of NGF (in vivo or in vitro) such that there is less NGF activity when compared to the absence of the antigen-binding molecule.

In an embodiment, the antigen-binding molecule, as described herein, is conjugated to another molecule or moiety, including functional moieties (e.g., toxins), detectable moieties (e.g., fluorescent molecules, radioisotopes), small molecule drugs and polypeptides.

The term "antibody", as used herein, is understood to mean any antigen-binding molecule or molecular complex comprising at least one complementarity determining region (CDR) that binds specifically to, or interacts specifically with, the target antigen. The term "antibody" includes full-length immunoglobulin molecules comprising two heavy (H) chains and two light (L) chains inter-connected by disulfide bonds, as well as multimers thereof (e.g., IgM). Each heavy chain comprises a heavy chain variable region (which may be abbreviated as HCVR, VH or $V_H$) and a heavy chain constant region. The heavy chain constant region typically comprises three domains—$C_H1$, $C_H2$ and $C_H3$. Each light chain comprises a light chain variable region (which may be abbreviated as LCVR, VL, VK, $V_K$ or $V_L$) and a light chain constant region. The light chain constant region will typically comprise one domain ($C_L1$). The $V_H$ and $V_L$ regions can be further subdivided into regions of hypervariability, termed complementarity determining regions (CDRs), interspersed with regions that are more conserved, also referred to as framework regions (FR). Each $V_H$ and $V_L$ typically comprises three CDRs and four FRs, arranged from amino-terminus to carboxy-terminus in the following order: FR1, CDR1, FR2, CDR2, FR3, CDR3, FR4. In some embodiments, the FRs of the antigen-binding molecules described herein may be identical to the FR of germline sequences of the target species (i.e., the species to which the antigen-binding molecules or antigen-binding fragments thereof, as described herein, will be administered). In some embodiments, the FR may be naturally or artificially modified. Whilst it is generally desirable that each of the FR sequences are identical to FR sequences derived from immunoglobulin molecules of the target species, including to minimize an immune response being raised against the binding molecule upon administration to a subject of the target species, in some embodiments, the antigen-binding molecule, or antigen-binding fragment thereof, may comprise one or more amino acid residues across one or more of its FR sequences that would be foreign at a corresponding position in one or more FR from the target species. Preferably, where the antigen-binding molecule, or antigen-binding fragment thereof, comprises one or more amino acid residues across one or more of its FR sequences that would be foreign at a corresponding position in the target species, that "foreign" amino acid residue will not (i) adversely impact the binding specificity of the antigen-binding molecule or antigen-binding fragment thereof to NGF, including native NGF and/or (ii) cause an immune response to be raised against the antigen-binding molecule or to the antigen-binding fragment thereof when administered to a subject of the target species.

Suitable antibodies include antibodies of any class, such as IgG, IgA, or IgM (including sub-classes thereof). There are five major classes of immunoglobulins: IgA, IgD, IgE, IgG, and IgM, characterised by heavy-chain constant regions a, 8, 8, Y, and u, respectively. Several antibody classes may be further divided into subclasses (isotypes), e.g., IgG1, IgG2, IgG3, IgG4, IgAQ1 and IgA2. The subunit structures and three-dimensional configurations of different classes of immunoglobulins will be well known to persons skilled in the art.

As used herein, the term "complementarity determining region" (CDR) refers to the region of an immunoglobulin variable domain that recognizes and binds to the target antigen. Each variable domain may comprises up to three CDR sequences, identified as CDR1, CDR2 and CDR3. The amino acid sequence of each CDR is often defined by Kabat numbering (e.g., about residues 24-34 (L1), 50-56 (L2) and 89-97 (L3) of the light chain variable domain and residues 31-35 (H1), 50-65 (H2) and 95-102 (H3) of the heavy chain variable domain; Kabat et al., Sequences of Proteins of Immunological Interest, 5th Ed. Public Health Service, National Institutes of Health, Bethesda, Md. (1991)) and/or by Chothia numbering (e.g., about residues 26-32 (L1), 50-52 (L2) and 91-96 (L3) of the light chain variable domain and 26-32 (H1), 53-55 (H2) and 96-101 (H3) of the heavy chain variable domain; see Chothia and Lesk J. Mol. Biol. 196:901-917 (1987)). As disclosed elsewhere herein, the present inventor has unexpectedly shown that amino acid positions along the CDR sequences of the NGF-binding molecules may be substituted with one or more conservative or non-conservative amino acids whilst retaining the ability to bind specifically to its target antigen, NGF. Hence, the present disclosure extends to functional variants of the NGF-binding molecules disclosed herein. The term "functional variant", as used herein, is to be understood as meaning an NGF-binding molecule comprising the CDR sequences having at least 70% sequence identity to SEQ ID NOs: 1-6 and retaining the ability to specifically bind to and neutralise or otherwise inhibit the activity of NGF.

The present disclosure extends to antigen-binding molecules that bind specifically to NGF of any species. In an embodiment, the NGF is selected from the group consisting of human NGF, canine NGF, feline NGF and equine NGF. In an embodiment, the NGF is a human NGF. In another embodiment, the NGF is a canine NGF. In another embodiment, the NGF is a feline NGF. In yet another embodiment, the NGF is an equine NGF. The present disclosure extends to antigen binding molecules that bind specifically to native NGF (i.e., naturally-occurring NGF), as well as to variants thereof. Such variants may include NGF molecules that differ from a naturally-occurring (wild-type) molecule by one or more amino acid substitutions, deletions and/or insertions. Variant NGF molecules of this type may be naturally-occurring or synthetic (e.g., recombinant) forms. It is to be understood, however, that in a preferred embodiment, the antigen-binding molecules described herein bind specifically to a native form of NGF, whether of a human or non-human species The terms "antigen-binding fragment", "antigen-binding portion", "antigen-binding domain", "antigen-binding site" and the like are used interchangeably herein to refer to a part of an antigen-binding molecule that retains the ability to bind to the target antigen; that is, to NGF, including native NGF. These terms include naturally occurring, enzymatically obtainable, synthetic or genetically engineered (recombinant) polypeptides and glycoproteins that specifically bind to NGF to form a complex.

Antigen-binding fragments may be derived, for example, from naturally-derived immunoglobulin molecules using any suitable method known to persons skilled in the art, illustrative examples of which include proteolytic digestion or recombinant genetic engineering techniques involving the manipulation and expression of nucleic acid sequences encoding antibody variable and optionally constant domains. Suitable nucleic acid sequences are known and/or are readily available from, e.g., commercial sources, DNA libraries (including, e.g., phage-antibody libraries), or can be synthesized. The nucleic acid sequences may be sequenced and manipulated chemically or by using molecular biology techniques, for example, to arrange one or more variable and/or constant domains into a suitable configuration, or to introduce codons, create cysteine residues, modify, add or delete amino acids, etc Non-limiting examples of suitable antigen-binding fragments include: (i) Fab fragments; (ii) F(ab') 2 fragments; (iii) Fd fragments; (iv) Fv fragments; (v) single-chain Fv (scFv) molecules; (vi) dAb fragments; and (vii) minimal recognition units consisting of the amino acid residues that mimic the hypervariable region of an antibody (e.g., an isolated CDR such as a CDR3 peptide), or a constrained FR3-CDR3-FR4 peptide. Other engineered molecules, such as domain-specific antibodies, single domain antibodies, domain-deleted antibodies, chimeric antibodies, CDR-grafted antibodies, one-armed antibodies, diabodies, triabodies, tetrabodies, minibodies, nanobodies (e.g. monovalent nanobodies, bivalent nanobodies, etc.), and small modular immunopharmaceuticals (SMIPs), are also encompassed by the term "antigen-binding fragment," as used herein.

In an embodiment, an antigen-binding fragment comprises at least one immunoglobulin variable domain. The variable domain may comprise an amino acid sequence of any suitable length or composition and will generally comprise at least one CDR which is adjacent to or in frame with one or more framework sequences. Where the antigen-binding fragment comprises a $V_H$ domain and a $V_L$ domain, the $V_H$ and $V_L$ domains may be situated relative to one another in any suitable arrangement. For example, the variable region may be dimeric and contain $V_H$-$V_H$, $V_H$-$V_L$ Or $V_L$-$V_L$ dimers. Alternatively, the antigen-binding fragment of an antibody may contain a monomeric $V_H$ or $V_L$ domain.

In some embodiments, an antigen-binding fragment may comprise at least one variable domain covalently linked to at least one constant domain. Non-limiting configurations of variable and constant domains that may be found within an antigen-binding fragment include: (i) $V_H$-$C_H1$; (ii) $V_H$-$C_H2$; (iii) $V_H$-$C_H3$; (iv) $V_H$-$C_H1$-$C_H2$; (v) $V_H$-$C_H1$-$C_H2$-$C_H3$, (vi) $V_H$-$C_H2$-$C_H3$; (vii) $V_H$-$C_L$; (viii) $V_L$-$C_H1$; (ix) $V_L$-$C_H2$, (x) $V_L$-$C_H3$; (xi) $V_L$-$C_H1$-$C_H2$; (xii) $V_L$-$C_H1$-$C_H2$-$C_H3$; (xiii) $V_L$-$C_H2$-$C_H3$; and (xiv) $V_L$-$C_L$. In any configuration of variable and constant domains, including any of the exemplary configurations listed above, the variable and constant domains may be either directly linked to one another or may be linked by a full or partial hinge or linker region. A hinge region may consist of at least 2 (e.g., 5, 10, 15, 20, 40, 60 or more) amino acids which result in a flexible or semi-flexible linkage between adjacent variable and/or constant domains in a single polypeptide molecule. In some embodiments, the antigen-binding fragment, as herein described, may comprise a homo-dimer or hetero-dimer (or other multimer) of any of the variable and constant domain configurations listed above in non-covalent association with one another and/or with one or more monomeric $V_H$ or $V_L$ domains (e.g., by disulfide bond(s)). A multispecific antigen-binding molecule will typically comprise at least two different variable domains, wherein each variable domain is capable of specifically binding to a separate antigen or to a different epitope on the same antigen. Any multispecific antigen-binding molecule format, including bispecific antigen-binding molecule formats, may be adapted for use in the context of an antigen-binding fragment of an antibody of the present disclosure using routine techniques available in the art.

The term "variable region" or "variable domain" refers to the domain of an immunoglobulin heavy or light chain that is involved in binding to the target antigen. The variable domains of the heavy chain and light chain ($V_H$ and $V_L$, respectively) of a native immunoglobulin molecule will generally have similar structures, with each domain comprising four conserved framework regions and three hypervariable regions (HVRs). See, e.g., Kindt et al., Kuby Immunology, 6th ed., W.H. Freeman and Co., page 91 (2007). A single $V_H$ or $V_L$ domain may be sufficient to confer antigen-binding specificity In a preferred embodiment, the antigen-binding molecule or antigen-binding fragment thereof is modified for compatibility with the target species. Thus, in an embodiment, the antigen-binding molecule or antigen-binding fragment thereof is humanized, caninized, felinized or equinized.

By "humanized" is meant that the antigen-binding molecule comprises an amino acid sequence that is compatible with humans, such that the amino acid sequence is unlikely to be seen as foreign by the immune system of a human subject. In an embodiment, the humanized antigen-binding molecule comprises one or more immunoglobulin framework regions derived from one or more human immunoglobulin molecules. In some embodiments, all of the framework regions of the humanized antigen-binding molecule will be derived from one or more human immunoglobulin molecules. The humanized antibody may optionally comprise an immunoglobulin heavy chain constant region derived from a human immunoglobulin molecule.

By "caninized" is meant that the antigen-binding molecule comprises an amino acid sequence that is compatible with canine, such that the amino acid sequence is unlikely to be seen as foreign by the immune system of a canine subject. In an embodiment, the caninized antigen-binding molecule comprises one or more immunoglobulin framework regions derived from one or more canine immunoglobulin molecules. In some embodiments, all of the framework regions of the caninized antigen-binding molecule will be derived from one or more canine immunoglobulin molecules. The caninized antibody may optionally comprise an immunoglobulin heavy chain constant region derived from a canine immunoglobulin molecule.

By "felinized" is meant that the antigen-binding molecule comprises an amino acid sequence that is compatible with feline, such that the amino acid sequence is unlikely to be seen as foreign by the immune system of a feline subject. In an embodiment, the felinized antigen-binding molecule comprises one or more immunoglobulin framework regions derived from one or more feline immunoglobulin molecules. In some embodiments, all of the framework regions of the felinized antigen-binding molecule will be derived from one or more feline immunoglobulin molecules. The felinized antibody may optionally comprise an immunoglobulin heavy chain constant region derived from a feline immunoglobulin molecule.

By "equinized" is meant that the antigen-binding molecule comprises an amino acid sequence that is compatible with equine, such that the amino acid sequence is unlikely to be seen as foreign by the immune system of an equine subject. In an embodiment, the equinized antigen-binding molecule comprises one or more immunoglobulin framework regions derived from one or more equine immunoglobulin molecules. In some embodiments, all of the framework regions of the equinized antigen-binding molecule will be derived from one or more equine immunoglobulin molecules. The equinized antibody may optionally comprise an immunoglobulin heavy chain constant region derived from an equine immunoglobulin molecule.

It is to be understood that the present disclosure also extends to antigen-binding molecules that are compatible with species other than human, canine, feline and equine. In this context, the antigen-binding molecules can be referred to as "speciesized", referring to the target species to which the molecule will be administered.

Suitable methods of designing and producing recombinant antibodies or antigen-binding molecules that are compatible with the target species will be familiar to persons skilled in the art, illustrative examples of which are described in Cattaneo (2010; supra), WO 2006/131951, WO 2012/153122, WO 2013/034900, WO 2012/153121 and WO 2012/153123, the contents of which are incorporated herein by reference in their entirety.

The phrase "specifically binds" or "specific binding" refers to a binding reaction between two molecules that is at least two times the background and more typically more than 10 to 100 times background molecular associations under physiological conditions. When using one or more detectable binding agents that are proteins, specific binding is determinative of the presence of the protein, in a heterogeneous population of proteins and other biologics. Thus, under designated immunoassay conditions, the specified antigen-binding molecule binds to a particular antigenic determinant, thereby identifying its presence. Specific binding to an antigenic determinant under such conditions requires an antigen-binding molecule that is selected for its specificity to that determinant. This selection may be achieved by subtracting out antigen-binding molecules that cross-react with other molecules. A variety of immunoassay formats may be used to select antigen-binding molecules (e.g., immunoglobulins) [such that they are specifically immunoreactive with a particular antigen. For example, solid-phase ELISA immunoassays are routinely used to select antibodies specifically immunoreactive with a protein (see, e.g., Harlow & Lane, Antibodies, A Laboratory Manual (1988) for a description of immunoassay formats and conditions that can be used to determine specific immunoreactivity). Methods of determining binding affinity and specificity are also well known in the art (see, for example, Harlow and Lane, supra); Friefelder, "Physical Biochemistry: Applications to biochemistry and molecular biology" (W.H. Freeman and Co. 1976))

"Affinity" or "binding affinity" refers to the strength of the sum total of non-covalent interactions between a single binding site of a molecule (e.g., an antigen-binding molecule) and its binding partner (e.g., an antigen). Unless indicated otherwise, as used herein, "binding affinity" refers to intrinsic binding affinity which reflects a 1:1 interaction between members of a binding pair e.g., an antigen-binding molecule. The affinity of a molecule X for its partner Y can generally be represented by the dissociation constant (Kd), which is the ratio of dissociation and association rate constants ($k_{off}$ and $k_{on}$, respectively). Thus, equivalent affinities may comprise different rate constants, as long as the ratio of the rate constants remains the same. Affinity can be measured by common methods known in the art, including those described herein. A particular method for measuring affinity is Surface Plasmon Resonance (SPR).

The terms "polypeptide", "peptide", or "protein" are used interchangeably herein to designate a linear series of amino acid residues connected one to the other by peptide bonds between the alpha-amino and carboxy groups of adjacent residues. The amino acid residues are usually in the natural "L" isomeric form. However, residues in the "D" isomeric form can be substituted for any L-amino acid residue, as long as the desired functional property is retained by the polypeptide As used herein, the term "modified antibody" includes synthetic forms of antibodies which are altered such that they are not naturally occurring, e.g., antibodies that comprise at least two heavy chain portions but not two complete heavy chains (such as domain deleted antibodies or minibodies); multispecific forms of antibodies (e.g., bispecific, trispecific, etc.) altered to bind to two or more different antigens or to different epitopes on a single antigen; heavy chain molecules joined to scFv molecules and the like. ScFv molecules are known in the art and are described, e.g., in U.S. Pat. No. 5,892,019. In addition, the term "modified antibody" includes multivalent forms of antibodies (e.g., trivalent, tetravalent, etc., antibodies that bind to three or more copies of the same antigen).

In one embodiment, the antigen-binding molecule comprises:

(a) a VHFR1 amino acid sequence having at least 80% sequence identity to a VHFR1 amino acid sequence selected from the group consisting of SEQ ID NO: 16, 20, 24, 28 and 32,
(b) a VHFR2 amino acid sequence having at least 80% sequence identity to a VHFR2 amino acid sequence selected from the group consisting of SEQ ID NO: 17, 21, 25, 29 and 33,
(c) a VHFR3 amino acid sequence having at least 80% sequence identity to a VHFR3 amino acid sequence selected from the group consisting of SEQ ID NO: 18, 22, 25, 30 and 34,
(d) a VHFR4 amino acid sequence having at least 80% sequence identity to a VHFR4 amino acid sequence selected from the group consisting of SEQ ID NO: 19, 23, 26, 31 and 35,
(e) a VLFR1 amino acid sequence having at least 80% sequence identity to a VLFR1 amino acid sequence selected from the group consisting of SEQ ID NO: 36, 40, 44 and 48,
(f) a VLFR2 amino acid sequence having at least 80% sequence identity to a VLFR2 amino acid sequence selected from the group consisting of SEQ ID NO, 37, 41, 45 and 49,
(g) a VLFR3 amino acid sequence having at least 80% sequence identity to a VLFR3 amino acid sequence selected from the group consisting of SEQ ID NO: 38, 42, 46 and 50,
(h) a VLFR4 amino acid sequence having at least 80% sequence identity to a VHFR4 amino acid sequence selected from the group consisting of SEQ ID NO: 39, 43, 47 and 51.

In one embodiment, the antigen binding molecule comprises a VH comprising VHFR1-VHFR4 and a VL comprising VLFR1-VLFR4 as shown in Table 3.

In one embodiment, the antigen-binding molecule comprises: (a) a VH amino acid sequence having at least 80% sequence identity to a VH amino acid sequence selected from the group consisting of SEQ ID NO: 7, SEQ ID NO: 8, SEQ ID NO: 9, SEQ ID NO: 10 and SEQ ID NO: 11, and (b) a VL amino acid sequence having at least 80% sequence identity to a VL amino acid sequence selected from the group consisting of SEQ ID NO: 12, SEQ ID NO; 13, SEQ ID NO: 14 and SEQ ID NO: 15.

In one embodiment, the antigen-binding molecule comprises: (a) a VH amino acid sequence having at least 80% sequence identity to at least one region other than a CDR region of a VH amino acid sequence selected from the group consisting of SEQ ID NO: 7, SEQ ID NO: 8, SEQ ID NO: 9, SEQ ID NO: 10 and SEQ ID NO: 11, and (b) a VL amino acid sequence having at least 80% sequence identity to at least one region other than a CDR region of a VL amino acid sequence selected from the group consisting of SEQ ID NO: 12, SEQ ID NO; 13, SEQ ID NO: 14 and SEQ ID NO: 15.

In an embodiment, the antigen-binding molecule comprises:

(a) a VH amino acid sequence of SEQ ID NO: 7 and a VL amino acid sequence of SEQ ID NO: 12,
(b) a VH amino acid sequence of SEQ ID NO: 7 and a VL amino acid sequence of SEQ ID NO: 13,
(c) a VH amino acid sequence of SEQ ID NO: 7 and a VL amino acid sequence of SEQ ID NO: 14,
(d) a VH amino acid sequence of SEQ ID NO: 7 and a VL amino acid sequence of SEQ ID NO: 15,
(e) a VH amino acid sequence of SEQ ID NO: 8 and a VL amino acid sequence of SEQ ID NO: 12,
(f) a VH amino acid sequence of SEQ ID NO: 8 and a VL amino acid sequence of SEQ ID NO: 13,
(g) a VH amino acid sequence of SEQ ID NO: 8 and a VL amino acid sequence of SEQ ID NO: 14,
(h) a VH amino acid sequence of SEQ ID NO: 8 and a VL amino acid sequence of SEQ ID NO: 15,
(i) a VH amino acid sequence of SEQ ID NO: 9 and a VL amino acid sequence of SEQ ID NO: 12,
(j) a VH amino acid sequence of SEQ ID NO: 9 and a VL amino acid sequence of SEQ ID NO: 13,
(k) a VH amino acid sequence of SEQ ID NO: 9 and a VL amino acid sequence of SEQ ID NO: 14,
(1) a VH amino acid sequence of SEQ ID NO: 9 and a VL amino acid sequence of SEQ ID NO: 15,
(m) a VH amino acid sequence of SEQ ID NO: 10 and a VL amino acid sequence of SEQ ID NO: 12,
(n) a VH amino acid of SEQ ID NO: 10 and a VL amino acid sequence having of SEQ ID NO: 13,
(o) a VH amino acid sequence of SEQ ID NO: 10 and a VL amino acid sequence of SEQ ID NO: 14,
(p) a VH amino acid sequence of SEQ ID NO: 10 and a VL amino acid sequence of SEQ ID NO: 15,
(q) a VH amino acid of SEQ ID NO: 11 and a VL amino acid sequence having of SEQ ID NO: 12,
(r) a VH amino acid sequence of SEQ ID NO: 11 and a VL amino acid sequence of SEQ ID NO: 13,
(s) a VH amino acid sequence of SEQ ID NO: 11 and a VL amino acid sequence of SEQ ID NO: 14, or
(t) a VH amino acid sequence of SEQ ID NO: 11 and a VL amino acid sequence of SEQ ID NO 15.

In another embodiment, the antigen-binding molecule comprises:

(a) a VHFR1 amino acid sequence having at least 80% sequence identity to a VHFR1 amino acid sequence of SEQ ID NO: 54,
(b) a VHFR2 amino acid sequence having at least 80% sequence identity to a VHFR2 amino acid of SEQ ID NO: 55,
(c) a VHFR3 amino acid sequence having at least 80% sequence identity to a VHFR3 amino acid sequence of SEQ ID NO: 56,
(d) a VHFR4 amino acid sequence having at least 80% sequence identity to a VHFR4 amino acid sequence of SEQ ID NO: 57,
(e) a VLFR1 amino acid sequence having at least 80% sequence identity to a VLFR1 amino acid sequence of SEQ ID NO:58,
(f) a VLFR2 amino acid sequence having at least 80% sequence identity to a VLFR2 amino acid sequence of SEQ ID NO:59,
(g) a VLFR3 amino acid sequence having at least 80% sequence identity to a VLFR3 amino acid sequence of SEQ ID NO: 60,
(h) a VLFR4 amino acid sequence having at least 80% sequence identity to a VHFR4 amino acid sequence of SEQ ID NO: 61.

In an embodiment, the antigen-binding molecule comprises a VH comprising the amino acid sequences of SEQ ID NO: 54, 55, 56 and 57 and a VL comprising the amino acid sequences of SEQ ID NO: 58, 59, 60 and 61.

In an embodiment, the antigen-binding molecule comprises:

(a) a VH amino acid sequence having at least 80% sequence identity to a VH amino acid sequence of SEQ ID NO: 52, and
(b) a VL amino acid sequence having at least 80% sequence identity to a VL amino acid sequence of SEQ ID NO: 53.

In an embodiment, the antigen-binding molecule comprises:

(a) a VH amino acid sequence having at least 80% sequence identity to at least one region other than a CDR region of a VH amino acid sequence of SEQ ID NO: 52, and
(b) a VL amino acid sequence having at least 80% sequence identity to at least one region other than a CDR region of a VL amino acid sequence of SEQ ID NO: 53.

In another embodiment, antigen-binding molecule is an antibody or an antigen-binding fragment thereof, as described elsewhere herein. In an embodiment, the antigen-binding fragment is selected from the group consisting of a Fab fragment, scFab, Fab', a single chain variable fragment (scFv) and a one-armed antibody.

Also disclosed herein is a chimeric molecule comprising an NGF-binding molecule, as herein described, and a heterologous moiety. In some embodiments, the heterologous moiety may be a detectable moiety, a half-life extending moiety, or a therapeutic moiety. Thus, as used herein, a "chimeric" molecule is one which comprises one or more unrelated types of components or contains two or more chemically distinct regions which can be conjugated to each other, fused, linked, translated, attached via a linker, chemically synthesized, expressed from a nucleic acid sequence, etc. For example, a peptide and a nucleic acid sequence, a peptide and a detectable label, unrelated peptide sequences, and the like. In embodiments in which the chimeric molecule comprises amino acid sequences of different origin, the chimeric molecule includes (1) polypeptide sequences that are not found together in nature (i.e., at least one of the amino acid sequences is heterologous with respect to at least one of its other amino acid sequences), or (2) amino acid sequences that are not naturally adjoined. For example, a "chimeric" antibody" as used herein refers to an antibody in which a portion of the heavy and/or light chain is derived from a particular source or species, while the remainder of the heavy and/or light chain is derived from a different source or species.

Also disclosed herein is an isolated polynucleotide comprising a nucleic acid sequence encoding the NGF-binding molecules, as described herein.

The term "polynucleotide" or "nucleic acid" are used interchangeably herein to refer to a polymer of nucleotides, which can be mRNA, RNA, CRNA, cDNA or DNA. The term typically refers to polymeric form of nucleotides of at least 10 bases in length, either ribonucleotides or deoxynucleotides or a modified form of either type of nucleotide. The term includes single and double stranded forms of DNA.

Also disclosed herein is a vector that comprises a nucleic acid encoding the NGF-binding molecules, as described herein.

By "vector" is meant a nucleic acid molecule, preferably a DNA molecule derived, for example, from a plasmid, bacteriophage, or virus, into which a nucleic acid sequence may be inserted or cloned. A vector preferably contains one or more unique restriction sites and may be capable of autonomous replication in a defined host cell including a target cell or tissue or a progenitor cell or tissue thereof, or be integrable with the genome of the defined host such that the cloned sequence is reproducible. Accordingly, the vector may be an autonomously replicating vector, i.e., a vector that exists as an extrachromosomal entity, the replication of which is independent of chromosomal replication, e.g., a linear or closed circular plasmid, an extrachromosomal element, a minichromosome, or an artificial chromosome. The vector may contain any means for assuring self-replication. Alternatively, the vector may be one which, when introduced into the host cell, is integrated into the genome and replicated together with the chromosome(s) into which it has been integrated. A vector system may comprise a single vector or plasmid, two or more vectors or plasmids, which together contain the total DNA to be introduced into the genome of the host cell, or a transposon. The choice of the vector will typically depend on the compatibility of the vector with the host cell into which the vector is to be introduced. The vector may also include a selection marker such as an antibiotic resistance gene that can be used for selection of suitable transformants. Examples of such resistance genes are well known to those of skill in the art.

In one embodiment, the vector is an adeno-associated virus (AAV) vector that enables the NGF-binding molecule, as described herein, to be safely administered to subjects and to provide a persistent expression of the NGF-binding molecule in the subject.

Adeno-associated virus is a member of the Parvoviridae family and comprises a linear, single-stranded DNA genome of less than about 5,000 nucleotides. AAV requires co-infection with a helper virus (i.e., an adenovirus or a herpes virus), or expression of helper genes, for efficient replication. AAV vectors used for administration of therapeutic nucleic acids typically have approximately 96% of the parental genome deleted, such that only the terminal repeats (ITRs), which contain recognition signals for DNA replication and packaging, remain. This eliminates immunologic or toxic side effects due to expression of viral genes. In addition, delivering specific AAV proteins to producing cells enables integration of the AAV vector comprising AAV ITRs into a specific region of the cellular genome, if desired (see, e.g., U.S. Pat. Nos. 6,342,390 and 6,821,511). Host cells comprising an integrated AAV genome show no change in cell growth or morphology (see, for example, U.S. Pat. No. 4,797,368).

The AAV ITRs flank the unique coding nucleotide sequences for the non-structural replication (Rep) proteins and the structural capsid (Cap) proteins (also known as virion proteins (VPs)). The terminal 145 nucleotides are self-complementary and are organized so that an energetically stable intramolecular duplex forming a T-shaped hairpin may be formed. These hairpin structures function as an origin for viral DNA replication by serving as primers for the cellular DNA polymerase complex. The Rep genes encode the Rep proteins Rep78, Rep68, Rep52, and Rep40. Rep78 and Rep68 are transcribed from the p5 promoter, and Rep 52 and Rep40 are transcribed from the p19 promoter. The Rep78 and Rep68 proteins are multifunctional DNA binding proteins that perform helicase and nickase functions during productive replication to allow for the resolution of AAV termini (see, e.g., Im et al., *Cell,* 61:447-57 (1990)). These proteins also regulate transcription from endogenous AAV promoters and promoters within helper viruses (see, e.g., Pereira et al., *J. Virol.,* 71:1079-1088 (1997)). The other Rep proteins modify the function of Rep78 and Rep68. The cap genes encode the capsid proteins VP1, VP2, and VP3. The cap genes are transcribed from the p40 promoter.

Also disclosed herein is an expression construct comprising a nucleic acid sequence encoding the NGF-binding molecule, as described herein, operably linked to one or more regulatory sequences.

The term "construct" refers to a recombinant genetic molecule including one or more isolated nucleic acid sequences from different sources. Thus, constructs are chimeric molecules in which two or more nucleic acid sequences of different origin are assembled into a single nucleic acid molecule and include any construct that contains (1) nucleic acid sequences, including regulatory and coding sequences that are not found together in nature (i.e., at least one of the nucleotide sequences is heterologous with respect to at least one of its other nucleotide sequences), or (2) sequences encoding parts of functional RNA molecules or proteins not naturally adjoined, or (3) parts of promoters that are not naturally adjoined. Representative constructs include any recombinant nucleic acid molecule such as a plasmid, cosmid, virus, autonomously replicating polynucleotide molecule, phage, or linear or circular single stranded or double stranded DNA or RNA nucleic acid molecule, derived from any source, capable of genomic integration or autonomous replication, comprising a nucleic acid molecule where one or more nucleic acid molecules have been operably linked. Constructs of the present invention will generally include the necessary elements to direct expression of a nucleic acid sequence of interest that is also contained in the construct, such as, for example, a target nucleic acid sequence or a modulator nucleic acid sequence. Such elements may include control elements or regulatory sequences such as a promoter that is operably linked to (so as to direct transcription of) the nucleic acid sequence of interest, and often includes a polyadenylation sequence as well. Within certain embodiments of the invention, the construct may be contained within a vector. In addition to the components of the construct, the vector may include, for example, one or more selectable markers, one or more origins of replication, such as prokaryotic and eukaryotic origins, at least one multiple cloning site, and/or elements to facilitate stable integration of the construct into the genome of a host cell. Two or more constructs can be contained within a single nucleic acid molecule, such as a single vector, or can be contained within two or more separate nucleic acid molecules, such as two or more separate vectors. An "expression construct" generally includes at least a control sequence operably linked to a nucleotide sequence of interest. In this manner, for example, promoters in operable connection with the nucleotide sequences to be expressed are provided in expression constructs for expression in an organism or part thereof including a host cell. For the practice of the present invention, conventional compositions and methods for preparing and using constructs and host cells are well known to one skilled in the art, see for example, Molecular Cloning: A Laboratory Manual, 3rd edition Volumes 1, 2, and 3. J. F. Sambrook, D. W. Russell, and N. Irwin, Cold Spring Harbor Laboratory Press, 2000.

By "control element", "control sequence", "regulatory sequence" and the like, as used herein, is meant a nucleic acid sequence (e.g., DNA) necessary for expression of an operably linked coding sequence in a particular host cell. The control sequences that are suitable for prokaryotic cells for example, include a promoter, and optionally a cis-acting sequence such as an operator sequence and a ribosome binding site. Control sequences that are suitable for eukaryotic cells include transcriptional control sequences such as promoters, polyadenylation signals, transcriptional enhancers, translational control sequences such as translational enhancers and internal ribosome binding sites (IRES), nucleic acid sequences that modulate mRNA stability, as well as targeting sequences that target a product encoded by a transcribed polynucleotide to an intracellular compartment within a cell or to the extracellular environment.

Also disclosed herein is a host cell comprising the construct as defined herein.

The terms "host", "host cell", "host cell line" and "host cell culture" are used interchangeably and refer to cells into which exogenous nucleic acid has been introduced, including the progeny of such cells. Host cells include "transformants" and "transformed cells", which include the primary transformed cell and progeny derived therefrom without regard to the number of passages. Progeny may not be completely identical in nucleic acid content to a parent cell, but may contain mutations. Mutant progeny that have the same function or biological activity as screened or selected for in the originally transformed cell are included herein. A host cell is any type of cellular system that can be used to generate the antigen binding molecules of the present invention. Host cells include cultured cells, e.g., mammalian cultured cells, such as CHO cells, BHK cells, NSO cells, SP2/0 cells, YO myeloma cells, P3X63 mouse myeloma cells, PER cells, PER. C6 cells or hybridoma cells, yeast cells, insect cells, and plant cells, to name only a few, but also cells comprised within a transgenic animal, transgenic plant or cultured plant or animal tissue. In one embodiment, the host cell is a CHO or HEK293 cell line.

Methods for producing a modified NGF-binding molecule, as described herein, is provided, such methods comprising culturing the host cell disclosed herein and recovering the NGF-binding molecule from the host cell or culture medium Also disclosed herein is a pharmaceutical composition comprising the NGF-binding molecule or a vector, as described herein, and a pharmaceutically acceptable carrier.

By "pharmaceutically acceptable carrier" is meant a pharmaceutical vehicle comprised of a material that is not biologically or otherwise undesirable, i.e., the material may be administered to a subject along with the selected active agent without causing any or a substantial adverse reaction. Carriers may include excipients and other additives such as diluents, detergents, colouring agents, wetting or emulsifying agents, pH buffering agents, preservatives, and the like.

Representative pharmaceutically acceptable carriers include any and all solvents, dispersion media, coatings, surfactants, antioxidants, preservatives {e.g., antibacterial agents, antifungal agents), isotonic agents, absorption delaying agents, salts, preservatives, drugs, drug stabilizers, gels, binders, excipients, disintegration agents, lubricants, sweetening agents, flavoring agents, dyes, such like materials and combinations thereof, as would be known to one of ordinary skill in the art (see, for example, Remington's Pharmaceutical Sciences, 18th Ed. Mack Printing Company, 1990, pp. 1289-1329, incorporated herein by reference). Except insofar as any conventional carrier is incompatible with the active ingredient(s), its use in the pharmaceutical compositions is contemplated.

The pharmaceutical compositions may be in a variety of forms. These include, for example, liquid, semi-solid and solid dosage forms, such as liquid solutions (e.g., injectable and infusible solutions), dispersions or suspensions, liposomes and suppositories. The preferred form depends on the intended mode of administration and therapeutic application. Suitable pharmaceutical compositions may be administered intravenously, subcutaneously or intramuscularly. In some embodiments, the compositions are in the form of injectable or infusible solutions. A preferred mode of administration is parenteral (e.g., intravenous, subcutaneous, intraperitoneal, intramuscular). In specific embodiments, the pharmaceutical composition is administered by intravenous infusion or injection. In other embodiments, the pharmaceutical composition is administered by intramuscular or subcutaneous injection.

The phrases "parenteral administration" and "administered parenterally" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal, epidural and intrasternal injection and infusion.

Preparations for parenteral administration include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. In the subject invention, pharmaceutically acceptable carriers include, but are not limited to, 0.01-0.1M and preferably 0.05M phosphate buffer or 0.8% saline. Other common parenteral vehicles include sodium phosphate solutions, Ringer's dextrose, dextrose and sodium chloride, lactated Ringer's, or fixed oils. Intravenous vehicles include fluid and nutrient replenishers, electrolyte replenishers, such as those based on Ringer's dextrose, and the like. Preservatives and other additives can also be present such as for example, antimicrobials, antioxidants, chelating agents, and inert gases and the like.

More particularly, pharmaceutical compositions suitable for injectable use include sterile aqueous solutions (where water soluble) or dispersions and sterile powders for the extemporaneous preparation of sterile injectable solutions or dispersions. In such cases, the composition must be sterile and should be fluid to the extent that easy syringability exists. It should be stable under the conditions of manufacture and storage and will preferably be preserved against the contaminating action of microorganisms, such as bacteria and fungi. The carrier can be a solvent or dispersion medium containing, for example, water, ethanol, polyol (e.g., glycerol, propylene glycol, and liquid polyethylene glycol, and the like), and suitable mixtures thereof. The proper fluidity can be maintained, for example, by the use of a coating such as lecithin and/or by the maintenance of the required particle size. In specific embodiments, an agent of the present disclosure may be conjugated to a vehicle for cellular delivery. In these embodiments, the agent may be encapsulated in a suitable vehicle to either aid in the delivery of the agent to target cells, to increase the stability of the agent, or to minimize potential toxicity of the agent. As will be appreciated by a skilled artisan, a variety of vehicles are suitable for delivering an agent of the present disclosure. Non-limiting examples of suitable structured fluid delivery systems may include nanoparticles, liposomes, microemulsions, micelles, dendrimers and other phospholipid-containing systems. Methods of incorporating agents of the present disclosure into delivery vehicles are known in the art. Although various embodiments are presented below, it will be appreciate that other methods known in the art to incorporate an antigen-binding molecule, as described herein, into a delivery vehicle are contemplated.

Dosage regimens are adjusted to provide the optimum desired response (e.g., a therapeutic response). For example, a single bolus may be administered, several divided doses may be administered over time or the dose may be proportionally reduced or increased as indicated by the exigencies of the therapeutic situation. An antigen-binding molecule of the present disclosure can be administered on multiple occasions. Intervals between single dosages can be daily, weekly, monthly or yearly. Intervals can also be irregular as indicated by measuring blood levels of modified polypeptide or antigen in the patient. Alternatively, the antigen-binding molecule can be administered as a sustained release formulation, in which case less frequent administration is required. Dosage and frequency vary depending on the half-life of the polypeptide in the patient.

It may be advantageous to formulate compositions in dosage unit form for ease of administration and uniformity of dosage. Dosage unit form as used herein refers to physically discrete units suited as unitary dosages for the subjects to be treated; each unit contains a predetermined quantity of active compound calculated to produce the desired therapeutic effect in association with the required pharmaceutically acceptable carrier. The specification for the dosage unit forms of the invention are dictated by and directly dependent on (a) the unique characteristics of the active compound and the particular therapeutic effect to be achieved, and (b) the limitations inherent in the art of compounding such an active compound for the treatment of sensitivity in individuals.

Dosages and therapeutic regimens of the antigen-binding molecule can be determined by a skilled artisan. In certain embodiments, the antigen-binding molecule is administered by injection (e.g., subcutaneously or intravenously) at a dose of about 0.01 to 40 mg/kg, e.g., 0.01 to 0.1 mg/kg, e.g., about 0.1 to 1 mg/kg, about 1 to 5 mg/kg, about 5 to 25 mg/kg, about 10 to 40 mg/kg, or about 0.4 mg/kg. The dosing schedule can vary from e.g., once a week to once every 2, 3, or 4 weeks. In one embodiment, the antigen-binding molecule is administered at a dose from about 10 to 20 mg/kg every other week. An exemplary, non-limiting range for an effective amount of an antigen-binding molecule of the present disclosure is 0.01-5 mg/kg, more suitably 0.03-2 mg/kg.

It is to be noted that dosage values may vary with the type and severity of the condition to be alleviated. It is to be further understood that for any particular subject, specific dosage regimens should be adjusted over time according to the individual need and the professional judgment of the person administering or supervising the administration of the compositions, and that dosage ranges set forth herein are exemplary only and are not intended to limit the scope or practice of the claimed composition.

The pharmaceutical compositions of the invention may include an effective amount of agent (i.e., the NGF-binding molecule) disclosed herein. The effective amount may be a "therapeutically effective amount" or a "prophylactically effective amount". A "therapeutically effective amount" refers to an amount effective, at dosages and for periods of time necessary, to achieve the desired therapeutic result. A therapeutically effective amount of the agent may vary according to factors such as the disease state, age, sex, and weight of the individual, and the ability of the agent to elicit a desired response in the individual. A therapeutically effective amount is also one in which any toxic or detrimental effects of the agent is outweighed by the therapeutically beneficial effects. Alternatively, this property of a composition can be evaluated by examining the ability of the compound to inhibit, for example in in vitro by assays known to the skilled practitioner.

By contrast, a "prophylactically effective amount" refers to an amount effective, at dosages and for periods of time necessary, to achieve the desired prophylactic result. Typically, since a prophylactic dose is used in subjects prior to or at an earlier stage of disease, the prophylactically effective amount will be less than the therapeutically effective amount.

Also disclosed herein is a method of treating, inhibiting or ameliorating pain in a subject, the method comprising the step of administering the NGF-binding molecule, or vector, as described herein, to a subject in need thereof.

The term "treating" as used herein may refer to (1) delaying the appearance of one or more symptoms of the condition; (2) inhibiting the development of the condition or one or more symptoms of the condition; (3) relieving the condition, i.e., causing regression of the condition or at least one or more symptoms of the condition; and/or (4) causing a decrease in the severity of the condition or of one or more symptoms of the condition.

The terms "treating", "treatment" and the like, are used interchangeably herein to mean relieving, reducing, alleviating, ameliorating or otherwise inhibiting the condition, including one or more symptoms of the condition. The terms "prevent", "preventing", "prophylaxis", "prophylactic", "preventative" and the like are used interchangeably herein to mean preventing or delaying the onset of the condition, or the risk of developing the condition.

The terms "treating", "treatment" and the like also include relieving, reducing, alleviating, ameliorating or otherwise inhibiting the effects of the condition for at least a period of time. It is also to be understood that terms "treating", "treatment" and the like do not imply that the condition, or a symptom thereof, is permanently relieved, reduced, alleviated, ameliorated or otherwise inhibited and therefore also encompasses the temporary relief, reduction, alleviation, amelioration or otherwise inhibition of the condition, or of a symptom thereof.

The terms "subject", "patient", "host" or "individual" used interchangeably herein, refer to any subject, particularly a vertebrate subject, and even more particularly a mammalian subject, for whom therapy or prophylaxis is desired. Suitable vertebrate animals that fall within the scope of the invention include, but are not restricted to, any member of the subphylum Chordata including primates (e.g., humans, monkeys and apes, and includes species of monkeys such as from the genus *Macaca* (e.g., cynomolgus monkeys such as *Macaca fascicularis*, and/or rhesus monkeys (*Macaca* mulatta)) and baboon (Papio *ursinus*), as well as marmosets (species from the genus Callithrix), squirrel monkeys (species from the genus Saimiri) and tamarins (species from the genus Saguinus), as well as species of apes such as chimpanzees (Pan troglodytes)), rodents (e.g., mice rats, guinea pigs), lagomorphs (e.g., rabbits, hares), bovines (e.g., cattle), ovines (e.g., sheep), caprines (e.g., goats), porcines (e.g., pigs), equines (e.g., horses), canines (e.g., dogs), felines (e.g., cats), avians (e.g., chickens, turkeys, ducks, geese, companion birds such as *canaries*, budgerigars etc.), marine mammals (e.g., dolphins, whales), reptiles (snakes, frogs, lizards etc.), and fish. In one embodiment, the subject is a human subject. In another embodiment, the subject is a canine subject. In another embodiment, the subject is a feline subject. In another embodiment, the subject is an equine subject.

Conditions associated with an abnormal (e.g., increased) level and/or abnormal (e.g., increased) activity of NGF will be familiar to persons skilled in the art. In an embodiment disclosed herein, the condition is pain. In an embodiment, the pain is selected from the group consisting of neuropathic pain, inflammatory pain, pruritic pain, peri-operative, post-operative and/or post-surgical pain.

As herein defined, the term "pain" typically means an unpleasant sensory and emotional experience associated with actual or potential tissue damage or described in terms of such damage.

In relation to operative or post-operative pain, the US Animal Welfare Act (Animal Welfare Act 2002. AWA regulations, CFR, Title 9 (Animals and Animal Products), Chapter 1 (Animal and Plant Health Inspection Service, Department of Agriculture). Subchapter A (Animal Welfare), Parts 1-4) defines a painful procedure as any procedure that would reasonably be expected to cause more than slight or momentary pain or distress in a subject to which that procedure was applied, that is, pain in excess of that caused by injections or other minor procedures. Therefore, if an animal (e.g. a canine, feline or porcine subject) undergoes a painful surgical procedure, the animal should receive postoperative analgesics.

A subject may be experiencing significant or chronic pain as a result of an associated medical condition such as rheumatoid arthritis, osteoarthritis, inflammation or a cancerous or malignant condition.

Also provided herein is an antigen-binding molecule, or vector, as described herein, for use in treating, inhibiting or ameliorating pain in a subject.

Also provided herein is the use of the NGF-binding molecules, or vector, as described herein, in the manufacture of a medicament for treating, inhibiting or ameliorating a condition associated with an abnormal (e.g., increased) level and/or abnormal (e.g., increased) activity of NGF in a subject in need thereof. In an embodiment, the condition is pain. In another embodiment, the condition is pain associated with arthritis. In another embodiment, the condition is arthritis. Thus, also disclosed herein is a method of treating or preventing arthritis or an arthritic condition in a subject, the method comprising the step of administering the NGF-binding molecule, or the vector, or the pharmaceutical composition, as described herein, to a subject in need thereof.

In an embodiment, the arthritis or arthritic condition is selected from the group consisting of immune mediated polyarthritis, rheumatoid arthritis and osteoarthritis.

Also provided herein is the NGF-binding molecule, or vector, as described herein, for use in the treatment or prevention of arthritis or an arthritic condition in a subject.

Also provided herein is the use of the NGF-binding molecule, or vector, as described herein, in the manufacture of a medicament for the treatment or prevention of arthritis or an arthritic condition in a subject.

Also disclosed herein is a method of treating or preventing a condition caused by, associated with, or resulting from, an increased expression of NGF or increased sensitivity to NGF in a subject in need thereof, the method comprising the step of administering the NGF-binding molecule, or vector, as described herein, to a subject in need thereof.

Also disclosed herein is the NGF-binding molecule, or the vector, or the pharmaceutical composition, as described herein, for use in the treatment of a condition caused by, associated with, or resulting from, an increased expression of NGF or increased sensitivity to NGF in a subject.

The present disclosure also extends to the use of the NGF-binding molecule, or the vector, as described herein, in the manufacture of a medicament for the treatment of a condition caused by, associated with, or resulting from, an increased expression of NGF or increased sensitivity to NGF in a subject.

The present disclosure also extends to a method for the treatment or prevention of a tumour induced to proliferate by NGF and conditions associated therewith, the method comprising administering the NGF-binding molecule, or the vector, or the pharmaceutical composition, as described herein, to a subject in need thereof.

In one embodiment, the tumour is an osteosarcoma.

Also provided herein is the NGF-binding molecule, or the vector, or the pharmaceutical composition, as described herein, for use in the treatment or prevention of a tumour induced to proliferate by NGF and conditions associated therewith, in a subject in need thereof.

The present disclosure also extends to the use of the NGF-binding molecule, or the vector, as described herein, in the manufacture of a medicament for the treatment or prevention of a tumour induced to proliferate by NGF and conditions associated therewith, in a subject in need thereof.

The present disclosure also extends to a kit comprising the NGF-binding molecule, or the vector, or the pharmaceutical composition, as described herein.

Also disclosed herein is the use of the NGF-binding molecule, or the vector, as described herein, for detecting NGF in a sample.

As used herein, "and/or" refers to and encompasses any and all possible combinations of one or more of the associated listed items, as well as the lack of combinations when interpreted in the alternative (or).

As used in this application, the singular form "a," "an," and "the" include plural references unless the context clearly dictates otherwise. For example, the term "an agent" includes a plurality of agents, including mixtures thereof.

By "about" is meant a quantity, level, value, number, frequency, percentage, dimension, size, amount, weight or length that varies by as much 15, 14, 13, 12, 11, 10, 9, 8, 7, 6, 5, 4, 3, 2 or 1% to a reference quantity, level, value, number, frequency, percentage, dimension, size, amount, weight or length.

Throughout this specification and the statements which follow, unless the context requires otherwise, the word "comprise", and variations such as "comprises" and "comprising", will be understood to imply the inclusion of a stated integer or step or group of integers or steps but not the exclusion of any other integer or step or group of integers or steps.

The reference in this specification to any prior publication (or information derived from it), or to any matter which is known, is not, and should not be taken as an acknowledgment or admission or any form of suggestion that that prior publication (or information derived from it) or known matter forms part of the common general knowledge in the field of endeavour to which this specification relates.

Those skilled in the art will appreciate that the invention described herein is susceptible to variations and modifications other than those specifically described. It is to be understood that the invention includes all such variations and modifications which fall within the spirit and scope. The invention also includes all of the steps, features, compositions and compounds referred to or indicated in this specification, individually or collectively, and any and all combinations of any two or more of said steps or features.

Certain embodiments of the invention will now be described with reference to the following examples which are intended for the purpose of illustration only and are not intended to limit the scope of the generality hereinbefore described.

EXAMPLES

Example 1: In Vitro Characterization of a Felinized Anti-NGF Antibody (Fe1)

A feline anti-NGF monoclonal antibody was engineered and expressed in Chinese Hamster Ovary (CHO) cells having the heavy chain and light chain CDR sequences shown in Table 1. The amino acid sequences of the heavy chain and light chain variable regions of Fe1 are shown in Table 4. The amino acid sequences of the heavy chain and light chain framework regions of Fe1 are shown in Table 5. The amino acid sequences encoding the heavy chain and light chain of Fe1 are shown in Table 6. The nucleic acid sequences encoding the heavy chain and light chain of Fe1 are shown in Table 7.

ELISA plates were coated with 0.1 μg/ml mouse (murine) NGF (muNGF) and blocked with PBS/0.05% Tween 20/1% BSA. muNGF-coated wells were then incubated for 1 hour at room temperature with antibody preparations, diluted in PBS/0.05% Tween 20/1% BSA (100 μl/well). Antibody concentrations ranging from 100 ng/ml to 1.56 ng/ml were used to establish a binding curve. After washing, the plates were incubated with a 1/5,000 dilution of goat anti-feline IgG-HRP in PBS/0.05% Tween 20/1% BSA. Plates were washed with PBS/0.05% Tween 20 and developed by the addition of TMB substrate. Development was stopped by the addition of 2M $H_2SO_4$, absorbance read at 450 nm and background values were subtracted from the absorbance readings.

As shown in FIG. 1, the Fe1 monoclonal antibody bound to murine NGF with good affinity.

Example 2: In Vivo Pharmacokinetics of Fe1

Pharmacokinetic (PK) studies were conducted in healthy cats. Five animals were administered Fe1 subcutaneously (s.c.) at 2.0 mg/kg on Day 0 and Day 28. Serum concentrations of the Fe1 antibody were assessed over 56 days. The concentration of Fe1 in the serum was determined using an NGF-binding ELISA, as described in Example 1, above. Pharmacokinetic parameters were determined using PKsolver software.

Figure 2:
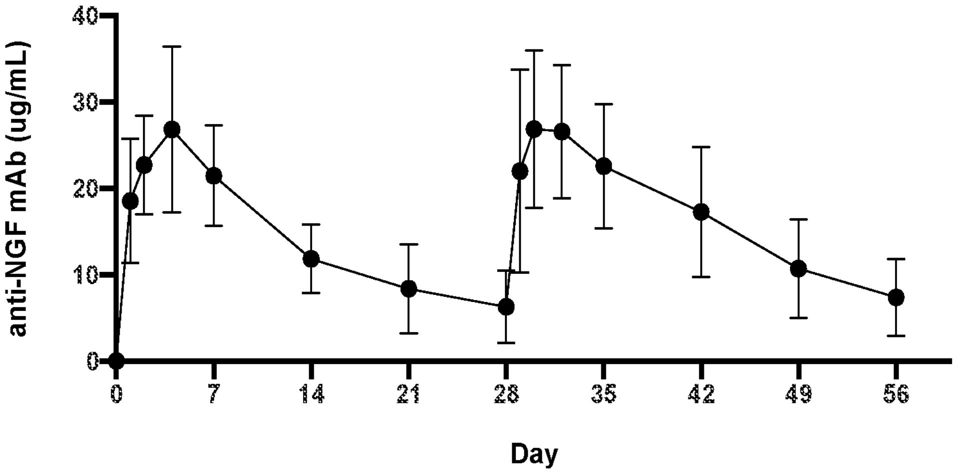
FIG. 2 shows the pharmacokinetic profile of Fe1 in cats following subcutaneous administration. Fe1 was administered subcutaneously twice to each of five cats at 2 mg/kg on Day 0 and Day 28. The serum concentration of Fe1 was determined at the times indicated using a quantitative NGF-binding ELISA, as described elsewhere herein. The data shown are mean±/−SD.

Fe1 exhibited a typical pharmacokinetic (PK) profile of an antibody administered subcutaneously (see FIG. 2). Following absorption from the site of injection, peak plasma levels (Cmax) were achieved at approximately 3-4 days (Tmax). The mean elimination half-life (T½) following the first dose was calculated to be 9 days (range 8-12 days). The second-dose PK profile was similar to the first, with T½ estimated to be 10 days (range 8-13 days). Following a second dose of Fe1 at Day 28, there was no change to the PK profile, indicating that no neutralising anti-Fe1 antibodies developed.

Example 3: In Vitro Characterization of Alternative Feline Anti-NGF Antibodies Three variants of the feline anti-NGF monoclonal antibodies (feNGFV5_1, feNGFV6_2 and feNGFV7_3) were engineered. The CDRs of the alternative variants were largely identical with the CDR sequences of Fe1 (also referred to herein as feNGF_JCV4), with the exception of single amino acid substitutions in one of the heavy chain CDR sequences, as shown in Table 8 (amino acid substitutions underlined).

Figure 3:
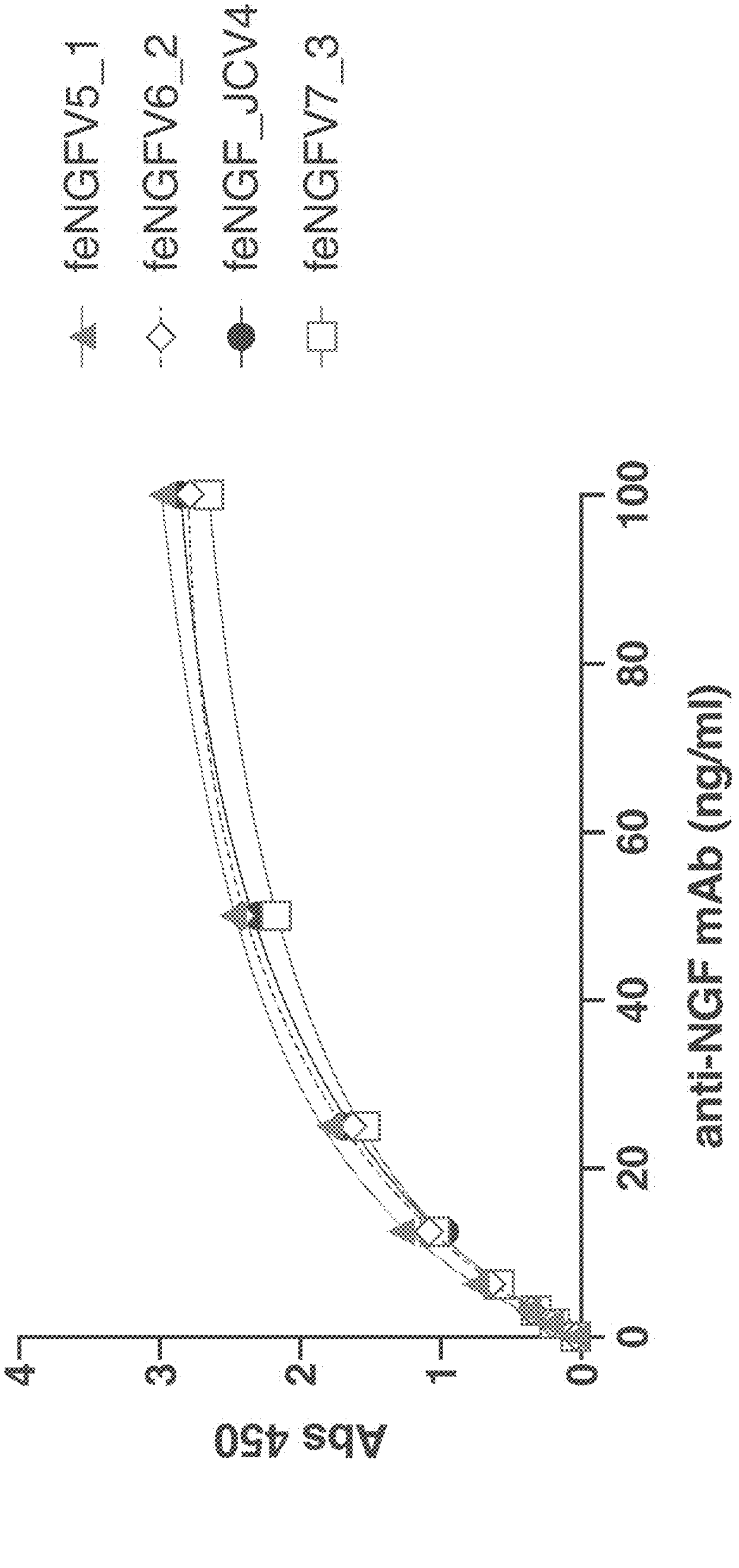
FIG. 3 shows binding of four feline anti-NGF antibody variants—Fe1 (feNGF_JCV4), feNGFV5_1, feNGFV6_2 and feNGFV7_3—to murine NGF, as determined by ELISA. The data shown are mean±/−SD.
Figure 4:
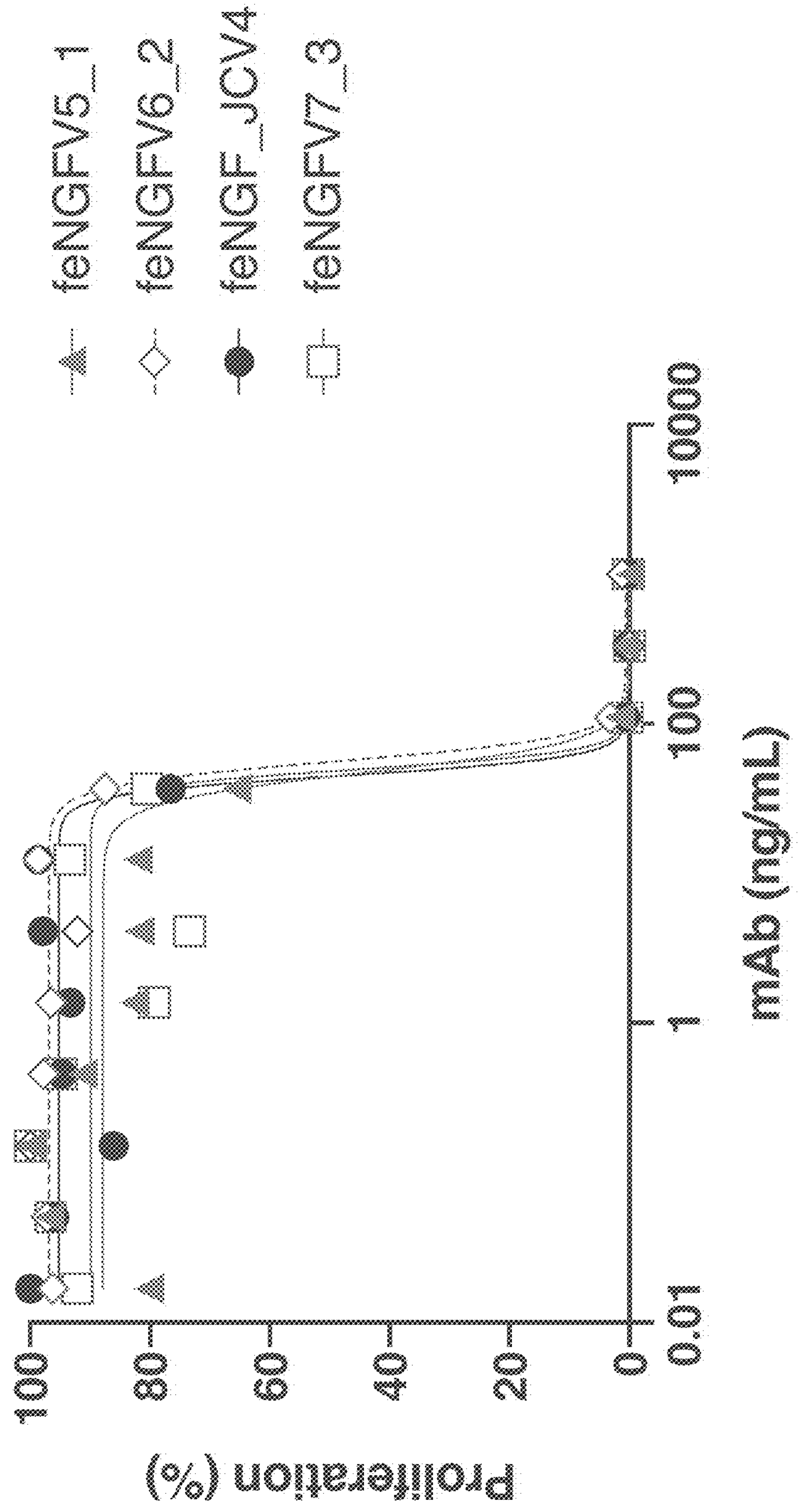
FIG. 4 shows the in vitro potency profile of the four feline anti-NGF antibody variants—Fe1 (feNGF_JCV4), feNGFV5_1, feNGFV6_2 and feNGFV7_3. TF-1 cells ($1\times10^5$ cells) were cultured in RPMI medium/10% fetal calf serum and 10 ng/mL NGF in the presence of increasing concentrations of the feline anti-NGF mAb variants for 48 hours at 37° C. Cell proliferation was determined using a colorimetric assay (CellTiter 96® AQueous One, Promega WI, USA). The data shown are mean±/−SD.

Evaluation of the feline anti-NGF mAb variants in binding and potency assays revealed that all three variants had similar binding properties (see FIGS. 3 and 4).

Example 4: In Vitro Characterization of Caninized Anti-NGF Monoclonal Antibodies, SCB01

The caninized anti-NGF mAb (SCB01; also referred to herein as Ca_NGF) was generated by germline grafting of CDRs into canine variable heavy and light chain framework regions. The heavy and light chain variable region amino acid sequences were compared against a database of canine germline variable and J segment sequences to identify the heavy and light chain canine sequences with the greatest degree of homology for use as canine variable domain frameworks. The closest matching germline was selected and then a series of caninized heavy and light chain variable regions were designed by grafting the CDR sequences onto the frameworks and, if necessary, by back-mutating residues identified from structural studies to rat residues which may be critical to the restoration of the antibody binding efficiency.

The amino acid sequences of heavy and light chain variable regions of the caninized anti-NGF antibody (SCB01) are as follows (the CDR sequences are highlighted by bold and underlined text):

SCB01_light chain variable region (SEQ ID NO: 15)

EIVMTQSPASLSLSQEEKVTITCRASEDIYNALA

WYQQKPGQAPKLLIYNTDTLHTGVPSRFSGSGSG

TDYSFTISSLEPEDVAVYFCQHYFHYPRTFGAGT

KVELK

SCB01_heavy chain variable region (SEQ ID NO: 11)

EVTLQESGPGLVKPSQTLSLTCVVSGLSLTNNNV

NWVRQRPGRGLEWMGGVWAGGATDYNSALKSRIS

ITRDTAKNQVSLQLSSMTTEDTAVYYCARDGGYS

SSTLYAMDAWGQGTLVTVSS

Example 5: In Vitro Characterization of Alternative Caninized Anti-NGF Antibodies Three variants of the caninized anti-NGF monoclonal antibodies (Ca_NGF_5, Ca_NGF_V62 and Ca_NGF_73)

were engineered. The CDRs of the alternative variants were largely identical with the CDR sequences of SCB01 (Ca_NGF), with the exception of single amino acid substitutions in one of the heavy chain CDR sequences, as shown in Table 9, below (amino acid substitutions underlined). A chimeric version of the rat anti-NGF monoclonal antibody (αD11), comprising the rat heavy and light chain variable region sequences as previously described in WO 2006/131951 fused to canine constant chain regions was also made as a control.

Figure 5:
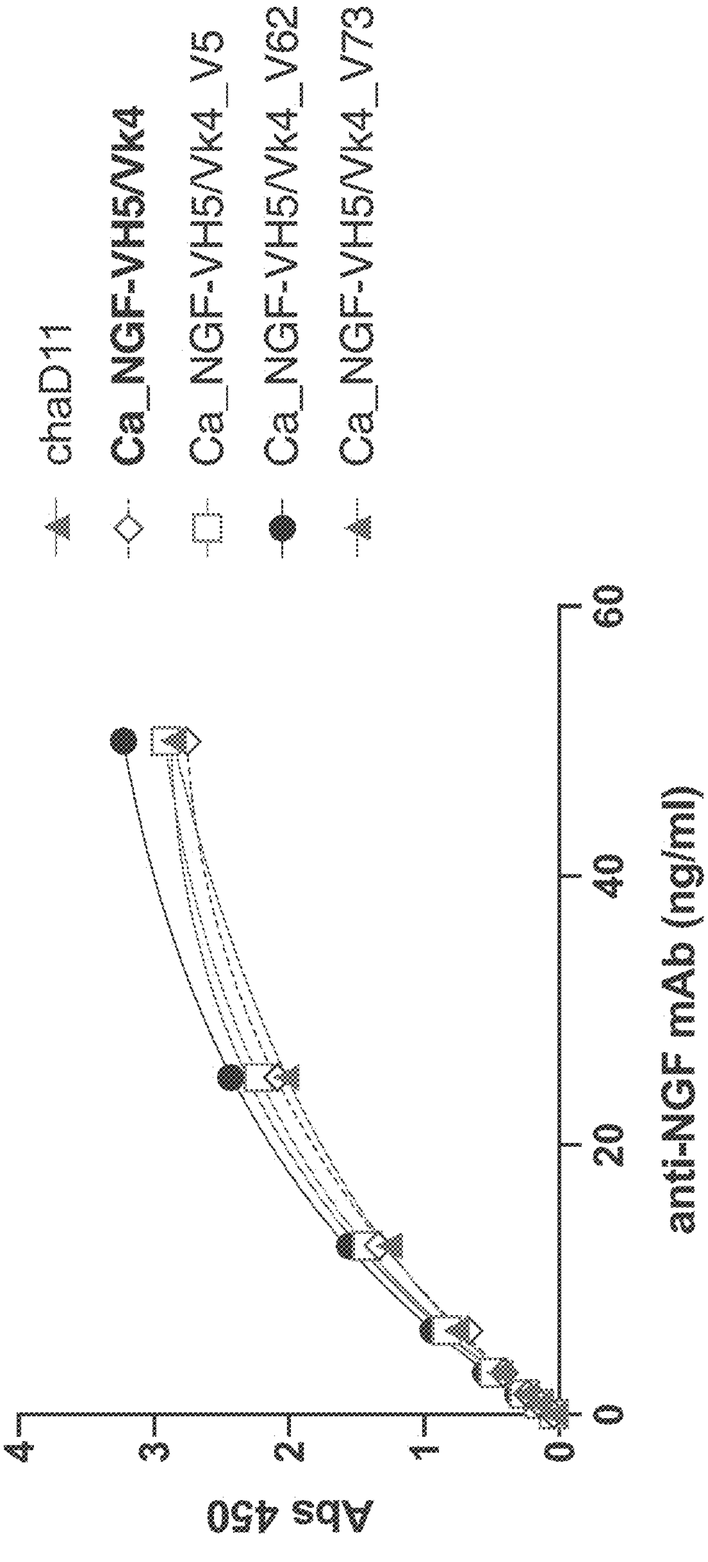
FIG. 5 shows binding of the caninized anti-NGF antibody (SCB01) to murine NGF, as determined by ELISA. The data shown are mean±/−SD.
Figure 6:
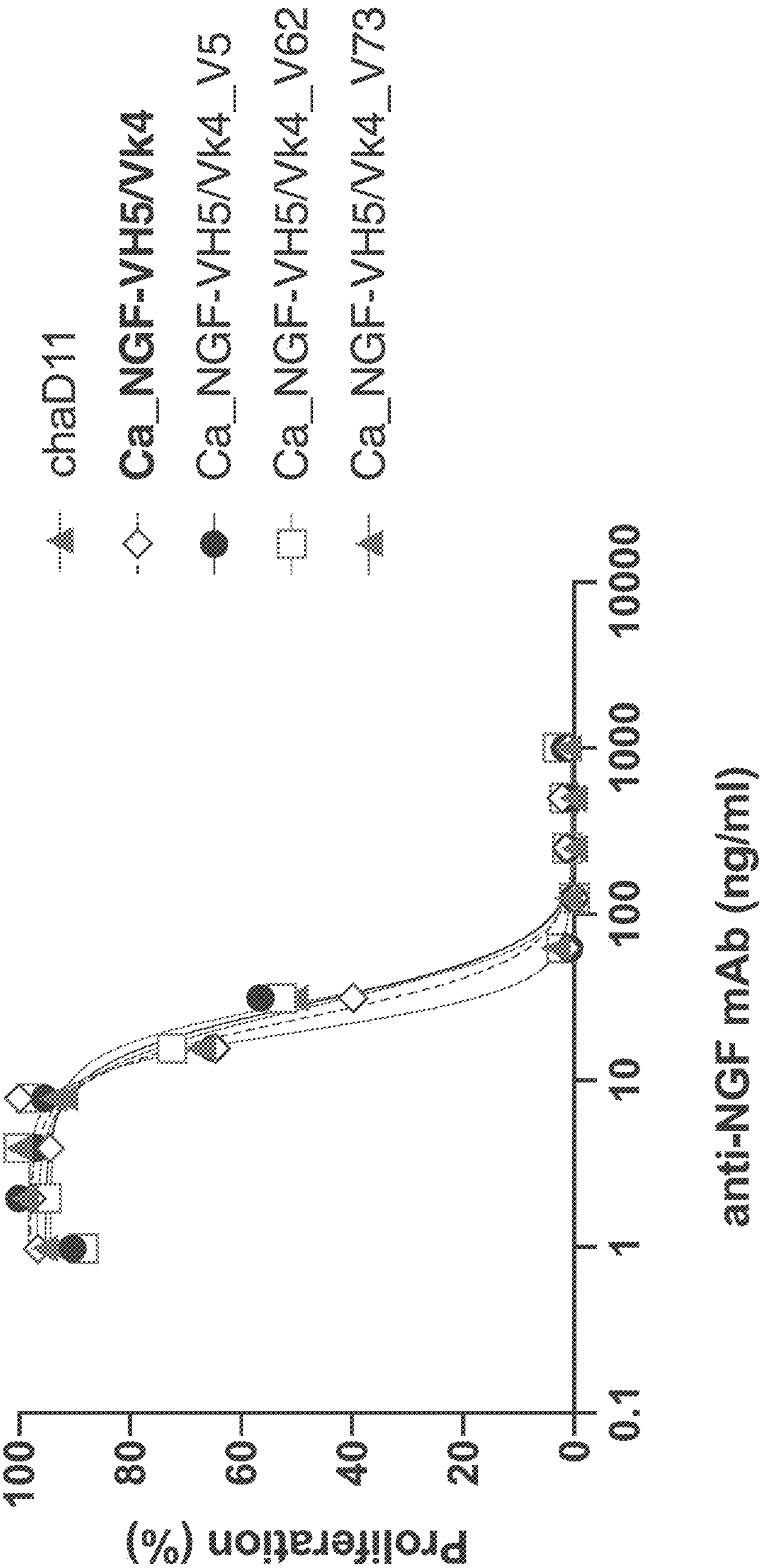
FIG. 6 shows the in vitro potency profile of four caninized anti-NGF antibody variants—SCB01 (Ca_NGF), Ca_NGF_5, Ca_NGF_62 and Ca_NGF_73. TF-1 cells ($1\times10^5$ cells) were cultured in RPMI medium/10% fetal calf serum and 10 ng/mL NGF in the presence of increasing concentrations of caninized anti-NGF mAb variants for 48 h at 37° C. Cell proliferation was determined using a colorimetric assay (CellTiter 96® AQueous One, Promega WI, USA). The data shown are mean±/−SD.

Evaluation of the caninized anti-NGF antibody variants in binding and potency assays revealed that each variant had similar binding properties (see FIGS. 5 and 6).

Example 6: Evaluation of Recombinant Production of Caninized Anti-NGF Antibody Variants In Vitro Caninized anti-NGF monoclonal antibodies were generated by selectively changing various framework residues from the rat parental sequence to amino acids commonly found in canine frameworks.

Two amino acid changes to the heavy chain CDR1 sequence were evaluated alone and in combination (Table 10) to assess the effect of the amino acid modifications on NGF binding and on recombinant antibody expression.

Full length canine antibodies (with the various alterations) and a chimeric version of αD11 (as described in WO 2006/131951), comprising the original rat variable heavy and light chain sequences fused to canine constant chain regions was also made as a control.

Purified antibodies were assessed for their ability to bind NGF using Surface Plasmon Resonance (SPR). All variants retained the high affinity binding to NGF (see Table 11), demonstrating a $K_D$ of ~1 μM.

Figure 7:
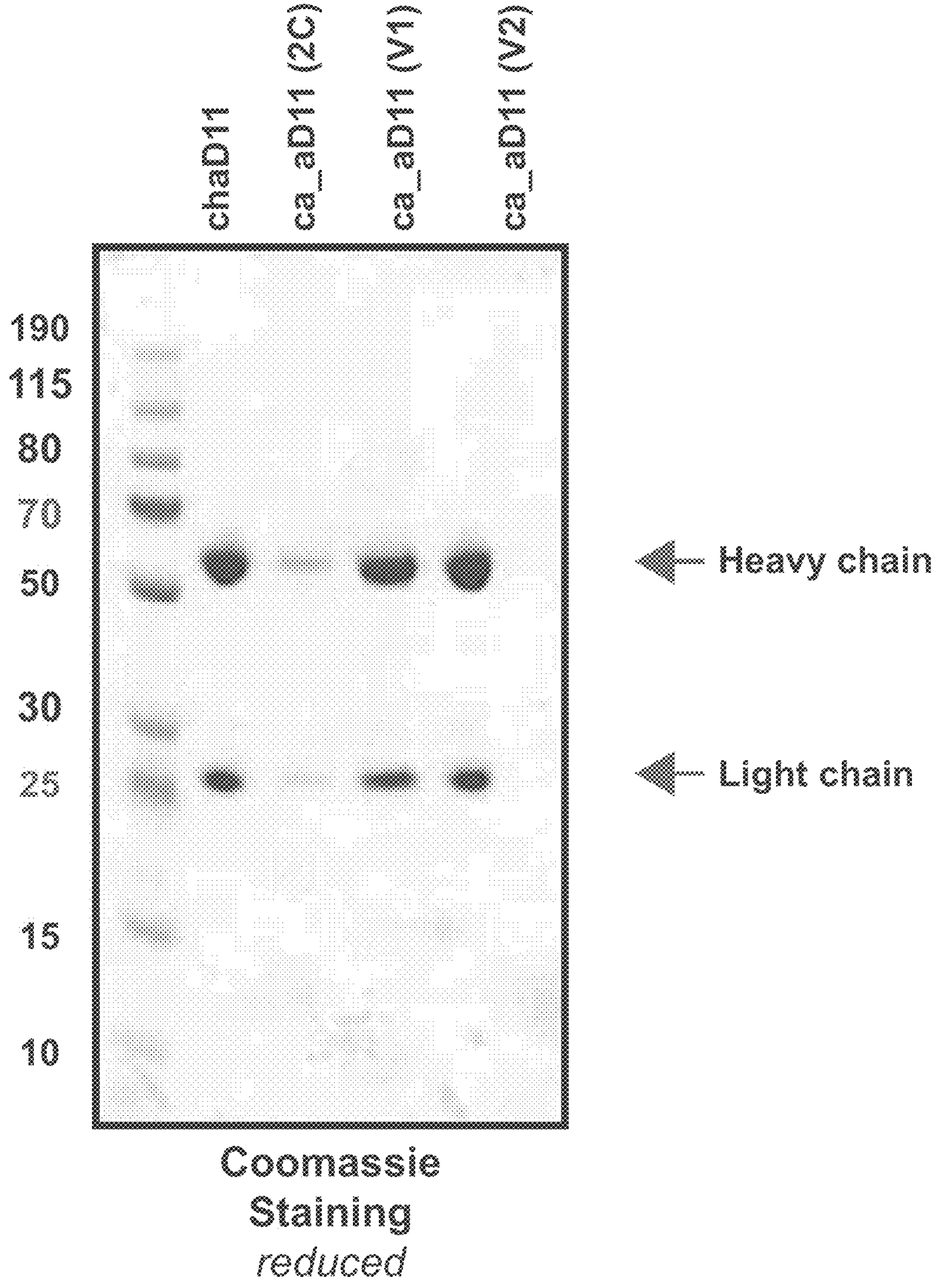
FIG. 7 shows an SDS-PAGE gel of purified recombinant caninized anti-NGF antibody variants and chimeric αD11 (mAb; CDR1: GFSLTNNNVN; SEQ ID NO: 69); Caninized αD11 (variant 2c; CDR1: TLSLTNNNVN; SEQ ID NO: 93); Caninized αD11 (variant V1; TFSLTNNNVN; SEQ ID NO: 94) and Caninized αD11 (variant V2; CDR1: GLSLTNNNVN; SEQ ID NO: 1). Each variant otherwise shared the same VH CDR2-3 and VL CDR1-3 sequences.

In the process of producing recombinant material for further studies, it was noted that there was a difference in the expression of the caninized anti-NGF antibody variants from transfected tissue culture cells. In vitro expression data in both small scale suspension and adherent systems demonstrated that the caninized αD11(2c) and caninized αD11 (V1) produced substantially less material than the chimeric and V2 variants and that the V2 variant seemed better than the original chimeric (see Table 12 and FIG. 7).

Table 1 shows the amino acid sequences of the CDRs of the NGF-binding molecules described herein (according to Kabat numbering):

VH CDR1 (SEQ ID NO: 1)
GLSLTNNNVN

VH CDR2 (SEQ ID NO: 2)
GVWAGGATDYNSA-$X_1$-KS

VH CDR3 (SEQ ID NO: 3)
DGGYSSSTLYAM-$X_2$-$X_3$

VL CDR1 (SEQ ID NO: 4)
RASEDIYNALA

VL CDR2 (SEQ ID NO: 5)
NTDTLHT

-continued

VL CDR3 (SEQ ID NO: 6)
QHYFHYPRT wherein $X_1$ is leucine or a conservative amino acid substitution thereof;

wherein $X_2$ is aspartic acid or a conservative amino acid substitution thereof; and wherein $X_3$ is alanine or a conservative amino acid substitution thereof.

Table 2 shows the amino acid sequences of the heavy chain (VH) and light chain (VL) variable regions of embodiments of caninized anti-NGF antibodies described herein:

| | Caninized VH Sequences |
|---|---|
| VH1 | QVQLQESGPGLVKPSQTLSLTCTV<br>S**GLSLTNNNV**NWVRQRTGRGLEW<br>MG**GVWAGGATDYNSALKS**RLSITR<br>DTAKSQVSLQMSSMTTEDTATYY<br>CAR**DGGYSSSTLYAMDA**WGQGTSV<br>TVSS (SEQ ID NO: 7) |
| VH2 | QVQLQESGPGLVKPSQTLSLTCTV<br>S**GLSLTNNNV**NWVRQRPGRGLEW<br>MG**GVWAGGATDYNSALKS**RLSITR<br>DTAKSQVSLQMSSMTTEDTATYY<br>CAR**DGGYSSSTLYAMDA**WGQGTLV<br>TVSS (SEQ ID NO: 8) |
| VH3 | QVQLQESGPGLVKPSQTLSLTCTV<br>S**GLSLTNNNV**NWVRQRPGRGLEW<br>MG**GVWAGGATDYNSALKS**RISITR<br>DTAKSQVSLQLSSMTTEDTATYY<br>CAR**DGGYSSSTLYAMDA**WGQGTLV<br>TVSS (SEQ ID NO: 9) |
| VH4 | EVTLQESGPGLVKPSQTLSLTCTV<br>S**GLSLTNNNV**NWVRQRPGRGLEW<br>MG**GVWAGGATDYNSALKS**RISITR<br>DTAKNQVSLQLSSMTTEDTATYY<br>CAR**DGGYSSSTLYAMDA**WGQGTLV<br>TVSS (SEQ ID NO: 10) |
| VH5 | EVTLQESGPGLVKPSQTLSLTCVV<br>S**GLSLTNNNV**NWVRQRPGRGLEW<br>MG**GVWAGGATDYNSALKS**RISITR<br>DTAKNQVSLQLSSMTTEDTAVYY<br>CAR**DGGYSSSTLYAMDA**WGQGTLV<br>TVSS (SEQ ID NO: 11) |
| | **Caninized VL Sequences** |
| VL1 | DIQMTQSPASLSLSQEEKVTITC<br>**RASEDIYNALA**WYQQKPGQAPKL<br>LIY**NTDTLHT**GVPSRFSGSGSGT<br>DYSFTISSLESEDVASYFC**QHYF**<br>**HYPRT**F<br>GAGTKVELK<br>(SEQ ID NO: 12) |
| VL2 | DIQMTQSPASLSLSQEEKVTITC<br>**RASEDIYNALA**WYQQKPGQAPKL<br>LIY**NTDTLHT**GVPSRFSGSGSGT<br>DYSFTISSLEPEDVASYFC**QHYF**<br>**HYPRT**F<br>GAGTKVELK<br>(SEQ ID NO: 13) |
| VL3 | EIVMTQSPASLSLSQEEKVTITC<br>**RASEDIYNALA**WYQQKPGQAPKL<br>LIY**NTDTLHT**GVPSRFSGSGSGT<br>DYSFTISSLEPEDVASYFC**QHYF**<br>**HYPRT**FGAGTKVELK<br>(SEQ ID NO: 14) |

-continued

| | |
|---|---|
| VL4 | EIVMTQSPASLSLSQEEKVTITC **RASEDIYNALA**WYQQKPGQAPKL LIY**NTDTLHT**GVPSRFSGSGSGT DYSFTISSLEPEDVAVYFC**QHYF HYPRT**FGAGTKVELK (SEQ ID NO: 15) |

Table 3 shows the framework region sequences of the caninized VH and VL sequences:

| | Caninized VH Framework Region Sequences |
|---|---|
| VH1 | FR1 QVQLQESGPGLVKPSQTLSLTCTVS (SEQ ID NO: 16) |
| | FR2 WVRQRTGRGLEWMG (SEQ ID NO: 17) |
| | FR3 RLSITRDTAKSQVSLQMSSMTTEDTATYYCAR (SEQ ID NO: 18) |
| | FR4 WGQGTSVTVSS (SEQ ID NO: 19) |
| VH2 | FR1 QVQLQESGPGLVKPSQTLSLTCTVS (SEQ ID NO: 20) |
| | FR2 WVRQRPGRGLEWMG (SEQ ID NO: 21) |
| | FR3 RLSITRDTAKSQVSLQMSSMTTEDTATYYCAR (SEQ ID NO: 22) |
| | FR4 WGQGTLVTVSS (SEQ ID NO: 23) |
| VH3 | FR1 QVQLQESGPGLVKPSQTLSLTCTVS (SEQ ID NO: 24) |
| | FR2 WVRQRPGRGLEWMG (SEQ ID NO: 25) |
| | FR3 RISITRDTAKSQVSLQLSSMTTEDTATYYCAR (SEQ ID NO: 26) |
| | FR4 WGQGTLVTVSS (SEQ ID NO: 27) |
| VH4 | FR1 EVTLQESGPGLVKPSQTLSLTCTVS (SEQ ID NO: 28) |
| | FR2 WVRQRPGRGLEWMG (SEQ ID NO: 29) |
| | FR3 RISITRDTAKNQVSLQLSSMTTEDTATYYCAR (SEQ ID NO: 30) |
| | FR4 WGQGTLVTVSS (SEQ ID NO: 31) |
| VH5 | FR1 EVTLQESGPGLVKPSQTLSLTCVVS (SEQ ID NO: 32) |
| | FR2 WVRQRPGRGLEWMG (SEQ ID NO: 33) |
| | FR3 RISITRDTAKNQVSLQLSSMTTEDTAVYYCAR (SEQ ID NO: 34) |
| | FR4 WGQGTLVTVSS (SEQ ID NO: 35) |
| | **Caninized VL Framework Region Sequences** |
| VLI | FR1 DIQMTQSPASLSLSQEEKVTITC (SEQ ID NO: 36) |
| | FR2 WYQQKPGQAPKLLIY (SEQ ID NO: 37) |
| | FR3 GVPSRFSGSGSGTDYSFTISSLESEDVASYFC (SEQ ID NO: 38) |
| | FR4 FGAGTKVELK (SEQ ID NO: 39) |
| VL2 | FR1: DIQMTQSPASLSLSQEEKVTITC (SEQ ID NO: 40) |
| | FR2:WYQQKPGQAPKLLIY (SEQ ID NO: 41) |
| | FR3:GVPSRFSGSGSGTDYSFTISSLEPEDVASYFC (SEQ ID NO: 42) |
| | FR4: FGAGTKVELK (SEQ ID NO: 43) |
| VL3 | FR1: EIVMTQSPASLSLSQEEKVTITC (SEQ ID NO: 44) |
| | FR2: WYQQKPGQAPKLLIY (SEQ ID NO: 45) |
| | FR3: GVPSRFSGSGSGTDYSFTISSLEPEDVASYFC (SEQ ID NO: 46) |
| | FR4: FGAGTKVELK (SEQ ID NO: 47) |
| VL4 | FR1: EIVMTQSPASLSLSQEEKVTITC (SEQ ID NO: 48) |
| | FR2: WYQQKPGQAPKLLIY (SEQ ID NO: 49) |
| | FR3: GVPSRFSGSGSGTDYSFTISSLEPEDVAVYFC (SEQ ID NO: 50) |
| | FR4: FGAGTKVELK (SEQ ID NO: 51) |

Table 4 shows the VH and VL sequences of the felinized anti-NGF antibody, Fe1.

VH Sequence (SEQ ID NO: 52)

QVQLMESGADLVQPSESLRLTCVASGLSLTNNNVNWVRQAPGKGLEW

MGGVWAGGATDYNSALKSRLTITRDTSKNTVFLQMHSLQSEDTATYY

CARDGGYSSSTLYAMDAWGQGTTVTVSA

VL Sequence (SEQ ID NO: 53)

DIEMTQSPLSLSATPGETVSISCRASEDIYNALAWYLQKPGRSPRLL

IYNTDTLHTGVPDRFSGSGSGTDFTLKISRVQTEDVGVYFCQHYFHY

PRTFGQGTKLELK

Table 5 shows the amino acid sequences of the heavy chain (VH1) and the light chain (VL) framework regions (FR1-4) of the felinized anti-NGF antibody, Fe1.

VH Framework Region Sequences

FR1:

(SEQ ID NO: 54)

QVQLMESGADLVQPSESLRLTCVAS

-continued

FR2:

(SEQ ID NO: 55)

WVRQAPGKGLEWMG

FR3:

(SEQ ID NO: 56)

RLTITRDTSKNTVFLQMHSLQSEDTATYYCAR

FR4:

(SEQ ID NO: 57)

WGQGTTVTVSA

VL Framework Region Sequences

FR1:

(SEQ ID NO: 58)

DIEMTQSPLSLSATPGETVSISC

FR2:

(SEQ ID NO: 59)

WYLQKPGRSPRLLIY

FR3:

(SEQ ID NO: 60)

GVPDRFSGSGSGTDFTLKISRVQTEDVGVYFC

FR4:

(SEQ ID NO: 61)

FGQGTKLELK

Table 6 shows exemplary amino sequences of the heavy and light chains of the felinized anti-NGF antibody, Fe1, for expression in CHO cells, including the signal sequence (underlined) and the constant region (italicized and underlined)

Heavy chain (HC) sequence

HC1

MEWSWVFLFFLSVTTGVHSQVQLME
SGADLVQPSESLRLTCVASGLSLTN
NNVNWVRQAPGKGLEWMGGVWAGGA
TDYNSALKSRLTITRDTSKNTVFLQ
MHSLQSEDTATYYCARDGGYSSSTL
YAMDAWGQGTTVTVSAASTTAPSVF
PIAPSCGTTSGATVALACLVLGYFP
EPVTVSWNSGALTSGVHTFPAVLQA
SGLYSLSSMVTVPSSRWLSDTFTCN
VAHPPSNTKVDKTVRKTDHPPGPKP
CDCPKCPPPEMLGGPSIFIFPPKPK
DTLSISRTPEVTCLVVDLGPDDSDV
QITWFVDNTQVYTAKTSPREEQFNS
TYRVVSVLPILHQDWLKGKEFKCKV
NSKSLPSPIERTISKAKGQPHEPQV
YVTPPAQEELSRNKVSVTCLIKSFH
PPDIAVEWEITGQPEPENNYRTTPP
QLDSDGTYFVYSKLSVDRSHWQRGN
TYTCSVSHEALHSHHTQKSLTQSPG
K
(SEQ ID NO: 62)

Light chain (LC) sequence

LC1

MSVPTQVLGLLLLWLTDARCDIEMT
QSPLSLSATPGETVSISCRASEDIY
NALAWYLQKPGRSPRLLIYNTDTLH
TGVPDRFSGSGSGTDFTLKISRVQT
EDVGVYFCQHYFHYPRTFGQGTKLE
LKRSDAQPSVFLFQPSLDELHTGSA
SIVCILNDFYPKEVNVKWKVDGVVQ
NKGIQESTTEQNSKDSTYSLSSTLT
MSSTEYQSHEKFSCEVTHKSLASTL
VKSFNRSECQRE
(SEQ ID NO: 63)

Table 7 shows exemplary nucleic acid sequences encoding the heavy and light chains of the felinized anti-NGF antibody, Fe1, for expression in CHO cells, including nucleic acid sequences encoding the signal sequence (underlined) and the constant region (italicised and underlined)

Heavy chain (HC) sequence

HC1

ATGGAATGGTCCTGGGTGTTCCTGT
TCTTCCTGTCTGTGACCACCGGCGT
GCACTCTCAGGTGCAGTTGATGGAA
TCTGGCGCCGACCTGGTGCAGCCTT
CTGAGTCTCTGAGACTGACCTGTGT
GGCCTCTGGACTGTCCCTGACCAAC
AACAACGTGAACTGGGTCCGACAGG
CTCCCGGCAAAGGATTGGAATGGAT
GGGCGGAGTTTGGGCTGGCGGCGCT
ACCGATTACAACTCTGCTCTGAAGT
CCCGGCTGACCATCACCAGAGACAC
CTCCAAGAACACCGTGTTTCTGCAG
ATGCACTCCCTGCAGTCTGAGGACA
CCGCCACCTACTACTGTGCTAGAGA
TGGCGGCTACTCCAGCAGCACCCTG
TACGCTATGGATGCTTGGGGCCAGG
GCACCACAGTGACAGTGTCTGCTGC
TTCTACCACCGCTCCTAGCGTTTTC
CCTCTGGCTCCTTCTTGTGGCACCA
CCTCTGGTGCTACAGTGGCTCTGGC
TTGTCTGGTGCTGGGCTACTTTCCT
GAGCCTGTGACCGTGTCTTGGAACT
CCGGTGCTCTGACATCTGGCGTGCA
CACCTTTCCAGCTGTGCTGCAGGCT
TCTGGCCTGTACTCTCTGTCCTCTA
TGGTCACCGTGCCTTCCAGCAGATG
GCTGTCCGACACCTTCACCTGTAAC
GTGGCCCATCCICCTAGCAACACCA
AGGTGGACAAGACCGTGCGCAAGAC
CGATCATCCTCCTGGACCTAAGCCT
TGCGACTGCCCTAAGTGTCCTCCAC
CTGAAATGCTCGGCGGACCCTCCAT
CTTCATCTTCCCACCTAAGCCAAAG
GACACCCTGTCCATCTCTCGGACCC
CTGAAGTCACCTGTCTGGTGGTGGA
TCTGGGCCCTGACGACTCTGATGTG
CAGATCACTTGGTTTGTGGACAATA
CCCAGGTCTACACCGCCAAGACCTC
TCCAAGAGAGGAACAGTTCAACTCC
ACCTACAGAGTGGTGTCCGTGCTGC
CCATCCTGCATCAGGATTGGCTGAA
GGGCAAAGAGTTCAAGTGCAAAGTG
AACTCCAAGAGCCTGCCTTCTCCAA
TCGAGCGGACCATCTCTAAGGCTAA
GGGCCAGCCTCATGAGCCCCAGGTT
TACTCTCCAATCGAGCGGACCATCT
CTAAGGCTAAGGGCCAGCCTCATGA
GCCCCAGGTTTACAAGAGCTTTCAC
CCTCCTGATATCGCCGTGGAATGGG
AGATCACAGGCCAGCCTGAGCCAGA
GAACAACTACAGAACCACACCTCCT
CAGCTGGACTCCGACGGCACCTACH
VGTGTACTCCAAGCTGTCCGTGGAC
AGATCCCACTGGCAGAGAGGCAACA
CCTATACCTGCTCTGTGTCTCACGA
GGCCCTGCACTCCCATCACACCCAG
AAGTCTCTGACCCAGTCTCCTGGCA
AGTGA
(SEQ ID NO: 64)

Light chain (LC) sequence

LC1

ATGTCCGTGCCTACACAGGTTCTGG
GACTGCTGCTGCTGTGGCTGACCGA
CGCTAGATGCGACATCGAGATGACC
CAGTCTCCACTGAGCCTGTCTGCTA
CACCTGGCGAGACAGTGTCCATCTC
CTGCAGAGCCTCCGAGGACATCTAC
AACGCCCTGGCCTGGTATCTGCAGA
AGCCTGGCAGATCCCCTCGGCTGCT
GATCTACAACACCGATACACTGCAC
ACCGGCGTGCCCGACAGATTTTCTG
GCTCTGGATCTGGCACCGACTTCAC
CCTGAAGATCTCCAGAGTGCAGACC

-continued

| |
|---|
| GAGGACGTGGGCGTGTACTTCTGCC |
| AGCACTACTTTCACTACCCTCGGAC |
| CTTTGGCCAGGGCACCAAGCTGGAA |
| CTGAAG*AGATCTGACGCCCAGCCTT* |
| *CCGTGTTCCTGTTCCAGCCTTCTCT* |
| *GGATGAGCTGCATACCGGCTCTGCC* |
| *TCCATCGTGTGCATCCTGAACGACT* |
| *TCTACCCCAAAGAAGTGAACGTGAA* |
| *GTGGAAGGTGGACGGCGTGGTGCAG* |
| *AACAAGGGCATCCAAGAGTCTACCA* |
| *CCGAGCAGAACTCCAAGGACTCCAC* |
| *CTACAGCCTGAGCAGCACCCTGACC* |
| *ATGTCCTCCACCGAGTACCAGAGCC* |
| *ACGAGAAGTTCAGCTGCGAAGTGAC* |
| *CCACAAGTCCCTGGCTTCTACCCTG* |
| *GTCAAGTCCTTCAACAGATCCGAGT* |
| *GCCAGCGCGTGA* |
| (SEQ ID NO: 65) |

Table 8 shows the CDR sequences of the heavy chain variable regions of the felinized anti-NGF antibody variants FeNGFV5, FeNGFV62 and FeNGFV73 for expression in CHO cells (amino acid substitutions are highlighted by bold and underlined text).

| | HC_CDR1 | HC_CDR2 | HC_CDR3 |
|---|---|---|---|
| Fel/ feNGF_JCV4 | GLSLTN NNVN (SEQ ID NO: 66) | GVWAGG ATDYNS ALKS (SEQ ID NO: 67) | DGGYSS STLYAM DA (SEQ ID NO: 68) |
| feNGFV5_1 | G**F**SLTN NNVN (SEQ ID NO: 69) | GVWAGG ATDYNS A**V**KS (SEQ ID NO: 70) | DGGYSS STLYAM DA (SEQ ID NO: 71) |
| feNGFV6_2 | G**F**SLTN NNVN (SEQ ID NO: 72) | GVWAGG ATDYNS ALKS (SEQ ID NO: 73) | DGGYSS STLYAM D**V** (SEQ ID NO: 74) |
| feNGFV7_3 | G**F**SLTN NNVN (SEQ ID NO: 75) | GVWAGG ATDYNS ALKS (SEQ ID NO: 76) | DGGYSS STLYAM **E**A (SEQ ID NO: 77) |

Table 9 shows the CDR sequences of the heavy chain variable region of the caninized anti-NGF antibody variants chαD11, SCB01 (Ca_NGF), Ca_NGF_V5, Ca_NGF_V62 and Ca_NGF_V73 for expression in CHO cells (amino acid substitutions are highlighted by bold and underlined text).

| | HC_CDR1 | HC_CDR2 | HC_CDR3 |
|---|---|---|---|
| chaD11 (chimeric αD11) | GFSLTN NNVN (SEQ ID NO: 78) | GVWAGG ATDYNS ALKS (SEQ ID NO: 79) | DGGYSS STLYAM DA (SEQ ID NO: 80) |
| Ca_NGF-VH5/Vk4 | GLSLTN NNVN (SEQ ID NO: 81) | GVWAGG ATDYNS ALKS (SEQ ID NO: 82) | DGGYSS STLYAM DA (SEQ ID NO: 83) |
| Ca_NGF_V5 | G**F**SLTN NNVN (SEQ ID NO: 84) | GVWAGG ATDYNS A**V**KS (SEQ ID NO: 85) | DGGYSS STLYAM DA (SEQ ID NO: 86) |
| Ca_NGF_V62 | G**F**SLTN NNVN (SEQ ID NO: 87) | GVWAGG ATDYNS ALKS (SEQ ID NO: 88) | DGGYSS STLYAM D**V** (SEQ ID NO: 89) |
| Ca_NGF_V73 | G**F**SLTN NNVN (SEQ ID NO: 90) | GVWAGG ATDYNS ALKS (SEQ ID NO: 91) | DGGYSS STLYAM **E**A (SEQ ID NO: 92) |

Table 10: shows the heavy chain CDR1 sequence of the parent antibody (αD11) and three caninized anti-NGF antibody variants—2c, V1 and V2 (amino acid substitutions are highlighted by bold and underlined text)

| | HC CDR 1 |
|---|---|
| αD11 (rat parental mAb) | GFSLTN NNVN (SEQ ID NO: 78) |
| Caninized αD11(2c) | **TL**SLIN NNVN (SEQ ID NO: 93) |
| Caninized αD11(V1) | **T**FSLTN NNVN (SEQ ID NO: 94) |
| Caninized αD11(V2) | G**L**SLTN NNVN (SEQ ID NO: 95) |

Table 11: shows the binding parameters of the caninized anti-NGF antibody variants beta muNGF binding constants determined at 39° C.

| | $k_a$ ($M^{-1}$ $s^{-1}$) | $k_d$ ($s^{-1}$) | $K_D$ (pM) |
|---|---|---|---|
| chimeric αD11 | 6.857(4)e6 | 6.20(6)e−6 | 0.905(6) |
| caninized αD11(2c) | 8.45(4)e6 | 9.76(7)e−6 | 1.15(1) |
| caninized αD11(V1) | 2.745(5)e6 | 4.76(4)e−6 | 1.73(2) |
| caninized αD11(V2) | 2.96(2)e6 | 4.1(2)e−6 | 1.4(1) |

The number in parentheses is the error in the last digit. For example, 6.857(4)e6 is (6.857±0.004)e6.

TABLE 12

Production yields of caninized anti-NGF antibody variants from small-scale in vitro culture (recombinant expression in CHO cells).

| | Total Protein |
|---|---|
| Chimeric αD11 mAb | 1.89 mg |
| Caninized αD11(2c) | 0.06 mg |
| Caninized αD11(V1) | 0.19 mg |
| Caninized αD11(V2) | 2.38 mg |

The invention claimed is:

1. An antigen-binding molecule that specifically binds to nerve growth factor (NGF), wherein the antigen-binding molecule comprises an immunoglobulin heavy chain variable domain (VH) and an immunoglobulin light chain variable domain (VL), wherein the VH comprises a complementarity determining region 1 (VH CDR1) comprising the amino acid sequence of SEQ ID NO: 1 (GLSLTNNNVN), a VH CDR2 comprising the amino acid sequence of SEQ ID NO: 2 (GVWAGGATDYNSA-X1-KS), and a VH CDR3 comprising the amino acid sequence of SEQ ID NO: 3 (DGGYSSSTLYAM-X2-X3); and wherein the VL comprises a complementarity determining region 1 (VL CDR1) comprising the amino acid sequence of SEQ ID NO: 4 (RASEDIYNALA), a VL CDR2 comprising the amino acid sequence of SEQ ID NO: 5 (NTDTLHT), and a VL CDR3 comprising the amino acid sequence of SEQ ID NO: 6 (QHYFHYPRT), wherein X1 is leucine or valine;

wherein X2 is aspartic acid or glutamic acid; and wherein X3 is alanine or valine.

2. The antigen-binding molecule of claim 1, wherein the antigen-binding molecule comprises:

(a) a VH framework region 1 (FR1) comprising an amino acid sequence having at least 80% sequence identity to an amino acid sequence selected from the group consisting of SEQ ID NO: 16, 20, 24, 28 and 32;

(b) a VH FR2 comprising an amino acid sequence having at least 80% sequence identity to an amino acid sequence selected from the group consisting of SEQ ID NO: 17, 21, 25, 29 and 33;

(c) a VH FR3 comprising an amino acid sequence having at least 80% sequence identity to an amino acid sequence selected from the group consisting of SEQ ID NO: 18, 22, 25, 30 and 34;

(d) a VH FR4 comprising an amino acid sequence having at least 80% sequence identity to an amino acid sequence selected from the group consisting of SEQ ID NO: 19, 23, 26, 31 and 35;

(e) a VL FR1 comprising an amino acid sequence having at least 80% sequence identity to an amino acid sequence selected from the group consisting of SEQ ID NO: 36, 40, 44 and 48;

(f) a VL FR2 comprising an amino acid sequence having at least 80% sequence identity to an amino acid sequence selected from the group consisting of SEQ ID NO, 37, 41, 45 and 49;

(g) a VL FR3 comprising an amino acid sequence having at least 80% sequence identity to an amino acid sequence selected from the group consisting of SEQ ID NO: 38, 42, 46 and 50; and (h) a VL FR4 comprising an amino acid sequence having at least 80% sequence identity to an amino acid sequence selected from the group consisting of SEQ ID NO: 39, 43, 47 and 51.

3. The antigen-binding molecule of claim 1, wherein:

(a) the VH comprises an amino acid sequence having at least 80% sequence identity to an amino acid sequence selected from the group consisting of SEQ ID NO: 7, SEQ ID NO: 8, SEQ ID NO: 9, SEQ ID NO: 10 and SEQ ID NO: 11, and (b) the VL comprises an amino acid sequence having at least 80% sequence identity to an amino acid sequence selected from the group consisting of SEQ ID NO: 12, SEQ ID NO; 13, SEQ ID NO: 14 and SEQ ID NO: 15.

4. The antigen-binding molecule of claim 1, wherein the antigen-binding molecule comprises:

(a) a VH FR1 comprising an amino acid sequence having at least 80% sequence identity to a VHFR1 amino acid sequence of SEQ ID NO: 54, (b) a VH FR2 comprising an amino acid sequence having at least 80% sequence identity to a VHFR2 amino acid of SEQ ID NO: 55, (c) a VH FR3 comprising an amino acid sequence having at least 80% sequence identity to a VHFR3 amino acid sequence of SEQ ID NO: 56, (d) a VH FR4 comprising an amino acid sequence having at least 80% sequence identity to a VHFR4 amino acid sequence of SEQ ID NO: 57, (e) a VL FR1 comprising an amino acid sequence having at least 80% sequence identity to a VLFR1 amino acid sequence of SEQ ID NO:58, (f) a VL FR2 comprising an amino acid sequence having at least 80% sequence identity to a VLFR2 amino acid sequence of SEQ ID NO:59, (g) a VL FR3 comprising an amino acid sequence having at least 80% sequence identity to a VLFR3 amino acid sequence of SEQ ID NO: 60, and (h) a VL FR4 comprising an amino acid sequence having at least 80% sequence identity to a VHFR4 amino acid sequence of SEQ ID NO: 61.

5. The antigen-binding molecule of claim 1, wherein the antigen-binding molecule comprises:

(a) the VH comprises an amino acid sequence having at least 80% sequence identity to a VH amino acid sequence of SEQ ID NO: 52, and (b) the VL comprises an amino acid sequence having at least 80% sequence identity to a VL amino acid sequence of SEQ ID NO: 53.

6. The antigen-binding molecule of claim 1, wherein the VH comprises a VH CDR1 comprising the amino acid sequence of SEQ ID NO: 66, a VH CDR2 comprising the amino acid sequence selected from the group consisting of SEQ ID NOs: 67, 70, 73 and 76 and a VH CDR3 comprising the amino acid sequence selected from the group consisting of SEQ ID NOs: 68, 71, 74 and 77.

7. The antigen-binding molecule of claim 1, wherein the VH comprises a VH CDR1 comprising the amino acid sequence of SEQ ID NO: 81, a VH CDR2 comprising the amino acid sequence selected from the group consisting of SEQ ID NOs: 82, 85, 88 and 91, and a VH CDR3 comprising the amino acid sequence selected from the group consisting of SEQ ID NOs: 83, 86, 89 and 92.

8. The antigen-binding molecule of claim 1, wherein the antigen-binding molecule is an antibody or an NGF-binding fragment thereof.

9. The antigen-binding molecule of claim 8, wherein the molecule is a humanized, caninized, felinized or equinized antibody.

10. A pharmaceutical composition comprising the antigen-binding molecule of claim 1, and a pharmaceutically acceptable carrier.

11. A method of inhibiting activity of NGF in a subject in need thereof, the method comprising administering to the subject the antigen-binding molecule of claim 1.

12. A method of inhibiting NGF-stimulated tumour proliferation in a subject in need thereof, the method comprising administering to a subject in need thereof the antigen-binding molecule of claim 1.

13. A method of inhibiting or reducing pain in a subject with arthritis, the method comprising administering to the subject the antigen-binding molecule of claim 1.

* * * * *

SEQUENCE LISTING

```
<160> NUMBER OF SEQ ID NOS: 95

<210> SEQ ID NO 1
<211> LENGTH: 10
<212> TYPE: PRT
<213> ORGANISM: rat rattus

<400> SEQUENCE: 1

Gly Leu Ser Leu Thr Asn Asn Asn Val Asn
1               5                   10


<210> SEQ ID NO 2
<211> LENGTH: 16
<212> TYPE: PRT
<213> ORGANISM: Artificial Sequence
<220> FEATURE:
<223> OTHER INFORMATION: NGF-binding molecule
<220> FEATURE:
<221> NAME/KEY: MISC_FEATURE
<222> LOCATION: (14)..(14)
<223> OTHER INFORMATION: Xaa is leucine or a conservative amino acid
      substitution thereof

<400> SEQUENCE: 2

Gly Val Trp Ala Gly Gly Ala Thr Asp Tyr Asn Ser Ala Xaa Lys Ser
1               5                   10                  15


<210> SEQ ID NO 3
<211> LENGTH: 14
<212> TYPE: PRT
<213> ORGANISM: Artificial Sequence
<220> FEATURE:
<223> OTHER INFORMATION: NGF-binding molecule
<220> FEATURE:
<221> NAME/KEY: MISC_FEATURE
<222> LOCATION: (13)..(13)
<223> OTHER INFORMATION: Xaa is aspartic acid or a conservative amino
      acid substitution thereof
<220> FEATURE:
<221> NAME/KEY: MISC_FEATURE
<222> LOCATION: (14)..(14)
<223> OTHER INFORMATION: Xaa is alanine or a conservative amino acid
      substitution thereof

<400> SEQUENCE: 3

Asp Gly Gly Tyr Ser Ser Ser Thr Leu Tyr Ala Met Xaa Xaa
1               5                   10


<210> SEQ ID NO 4
<211> LENGTH: 11
<212> TYPE: PRT
<213> ORGANISM: NGF-binding molecule

<400> SEQUENCE: 4

Arg Ala Ser Glu Asp Ile Tyr Asn Ala Leu Ala
1               5                   10


<210> SEQ ID NO 5
<211> LENGTH: 7
<212> TYPE: PRT
<213> ORGANISM: NGF-binding molecule

<400> SEQUENCE: 5

Asn Thr Asp Thr Leu His Thr
1               5


<210> SEQ ID NO 6
<211> LENGTH: 9
```

```
<212> TYPE: PRT
<213> ORGANISM: NGF-binding molecule

<400> SEQUENCE: 6

Gln His Tyr Phe His Tyr Pro Arg Thr
1               5


<210> SEQ ID NO 7
<211> LENGTH: 122
<212> TYPE: PRT
<213> ORGANISM: Artificial Sequence
<220> FEATURE:
<223> OTHER INFORMATION: Caninized anti-NGF

<400> SEQUENCE: 7

Gln Val Gln Leu Gln Glu Ser Gly Pro Gly Leu Val Lys Pro Ser Gln
1               5                   10                  15

Thr Leu Ser Leu Thr Cys Thr Val Ser Gly Leu Ser Leu Thr Asn Asn
            20                  25                  30

Asn Val Asn Trp Val Arg Gln Arg Thr Gly Arg Gly Leu Glu Trp Met
        35                  40                  45

Gly Gly Val Trp Ala Gly Gly Ala Thr Asp Tyr Asn Ser Ala Leu Lys
    50                  55                  60

Ser Arg Leu Ser Ile Thr Arg Asp Thr Ala Lys Ser Gln Val Ser Leu
65                  70                  75                  80

Gln Met Ser Ser Met Thr Thr Glu Asp Thr Ala Thr Tyr Tyr Cys Ala
                85                  90                  95

Arg Asp Gly Gly Tyr Ser Ser Ser Thr Leu Tyr Ala Met Asp Ala Trp
            100                 105                 110

Gly Gln Gly Thr Ser Val Thr Val Ser Ser
        115                 120


<210> SEQ ID NO 8
<211> LENGTH: 122
<212> TYPE: PRT
<213> ORGANISM: Artificial Sequence
<220> FEATURE:
<223> OTHER INFORMATION: Caninized anti-NGF

<400> SEQUENCE: 8

Gln Val Gln Leu Gln Glu Ser Gly Pro Gly Leu Val Lys Pro Ser Gln
1               5                   10                  15

Thr Leu Ser Leu Thr Cys Thr Val Ser Gly Leu Ser Leu Thr Asn Asn
            20                  25                  30

Asn Val Asn Trp Val Arg Gln Arg Pro Gly Arg Gly Leu Glu Trp Met
        35                  40                  45

Gly Gly Val Trp Ala Gly Gly Ala Thr Asp Tyr Asn Ser Ala Leu Lys
    50                  55                  60

Ser Arg Leu Ser Ile Thr Arg Asp Thr Ala Lys Ser Gln Val Ser Leu
65                  70                  75                  80

Gln Met Ser Ser Met Thr Thr Glu Asp Thr Ala Thr Tyr Tyr Cys Ala
                85                  90                  95

Arg Asp Gly Gly Tyr Ser Ser Ser Thr Leu Tyr Ala Met Asp Ala Trp
            100                 105                 110

Gly Gln Gly Thr Leu Val Thr Val Ser Ser
        115                 120


<210> SEQ ID NO 9
<211> LENGTH: 122
```

<212> TYPE: PRT
<213> ORGANISM: Artificial Sequence
<220> FEATURE:
<223> OTHER INFORMATION: Caninized anti-NGF

<400> SEQUENCE: 9

Gln Val Gln Leu Gln Glu Ser Gly Pro Gly Leu Val Lys Pro Ser Gln
1 5 10 15

Thr Leu Ser Leu Thr Cys Thr Val Ser Gly Leu Ser Leu Thr Asn Asn
20 25 30

Asn Val Asn Trp Val Arg Gln Arg Pro Gly Arg Gly Leu Glu Trp Met
35 40 45

Gly Gly Val Trp Ala Gly Gly Ala Thr Asp Tyr Asn Ser Ala Leu Lys
50 55 60

Ser Arg Ile Ser Ile Thr Arg Asp Thr Ala Lys Ser Gln Val Ser Leu
65 70 75 80

Gln Leu Ser Ser Met Thr Thr Glu Asp Thr Ala Thr Tyr Tyr Cys Ala
85 90 95

Arg Asp Gly Gly Tyr Ser Ser Ser Thr Leu Tyr Ala Met Asp Ala Trp
100 105 110

Gly Gln Gly Thr Leu Val Thr Val Ser Ser
115 120

<210> SEQ ID NO 10
<211> LENGTH: 122
<212> TYPE: PRT
<213> ORGANISM: Artificial Sequence
<220> FEATURE:
<223> OTHER INFORMATION: Caninized anti-NGF

<400> SEQUENCE: 10

Glu Val Thr Leu Gln Glu Ser Gly Pro Gly Leu Val Lys Pro Ser Gln
1 5 10 15

Thr Leu Ser Leu Thr Cys Thr Val Ser Gly Leu Ser Leu Thr Asn Asn
20 25 30

Asn Val Asn Trp Val Arg Gln Arg Pro Gly Arg Gly Leu Glu Trp Met
35 40 45

Gly Gly Val Trp Ala Gly Gly Ala Thr Asp Tyr Asn Ser Ala Leu Lys
50 55 60

Ser Arg Ile Ser Ile Thr Arg Asp Thr Ala Lys Asn Gln Val Ser Leu
65 70 75 80

Gln Leu Ser Ser Met Thr Thr Glu Asp Thr Ala Thr Tyr Tyr Cys Ala
85 90 95

Arg Asp Gly Gly Tyr Ser Ser Ser Thr Leu Tyr Ala Met Asp Ala Trp
100 105 110

Gly Gln Gly Thr Leu Val Thr Val Ser Ser
115 120

<210> SEQ ID NO 11
<211> LENGTH: 122
<212> TYPE: PRT
<213> ORGANISM: Artificial Sequence
<220> FEATURE:
<223> OTHER INFORMATION: Caninized anti-NGF

<400> SEQUENCE: 11

Glu Val Thr Leu Gln Glu Ser Gly Pro Gly Leu Val Lys Pro Ser Gln
1 5 10 15

```
Thr Leu Ser Leu Thr Cys Val Val Ser Gly Leu Ser Leu Thr Asn Asn
            20                  25                  30

Asn Val Asn Trp Val Arg Gln Arg Pro Gly Arg Gly Leu Glu Trp Met
        35                  40                  45

Gly Gly Val Trp Ala Gly Gly Ala Thr Asp Tyr Asn Ser Ala Leu Lys
    50                  55                  60

Ser Arg Ile Ser Ile Thr Arg Asp Thr Ala Lys Asn Gln Val Ser Leu
65                  70                  75                  80

Gln Leu Ser Ser Met Thr Thr Glu Asp Thr Ala Val Tyr Tyr Cys Ala
                85                  90                  95

Arg Asp Gly Gly Tyr Ser Ser Ser Thr Leu Tyr Ala Met Asp Ala Trp
            100                 105                 110

Gly Gln Gly Thr Leu Val Thr Val Ser Ser
        115                 120


<210> SEQ ID NO 12
<211> LENGTH: 107
<212> TYPE: PRT
<213> ORGANISM: Artificial Sequence
<220> FEATURE:
<223> OTHER INFORMATION: Caninized anti-NGF

<400> SEQUENCE: 12

Asp Ile Gln Met Thr Gln Ser Pro Ala Ser Leu Ser Leu Ser Gln Glu
1               5                   10                  15

Glu Lys Val Thr Ile Thr Cys Arg Ala Ser Glu Asp Ile Tyr Asn Ala
            20                  25                  30

Leu Ala Trp Tyr Gln Gln Lys Pro Gly Gln Ala Pro Lys Leu Leu Ile
        35                  40                  45

Tyr Asn Thr Asp Thr Leu His Thr Gly Val Pro Ser Arg Phe Ser Gly
    50                  55                  60

Ser Gly Ser Gly Thr Asp Tyr Ser Phe Thr Ile Ser Ser Leu Glu Ser
65                  70                  75                  80

Glu Asp Val Ala Ser Tyr Phe Cys Gln His Tyr Phe His Tyr Pro Arg
                85                  90                  95

Thr Phe Gly Ala Gly Thr Lys Val Glu Leu Lys
            100                 105


<210> SEQ ID NO 13
<211> LENGTH: 107
<212> TYPE: PRT
<213> ORGANISM: Artificial Sequence
<220> FEATURE:
<223> OTHER INFORMATION: Caninized anti-NGF

<400> SEQUENCE: 13

Asp Ile Gln Met Thr Gln Ser Pro Ala Ser Leu Ser Leu Ser Gln Glu
1               5                   10                  15

Glu Lys Val Thr Ile Thr Cys Arg Ala Ser Glu Asp Ile Tyr Asn Ala
            20                  25                  30

Leu Ala Trp Tyr Gln Gln Lys Pro Gly Gln Ala Pro Lys Leu Leu Ile
        35                  40                  45

Tyr Asn Thr Asp Thr Leu His Thr Gly Val Pro Ser Arg Phe Ser Gly
    50                  55                  60

Ser Gly Ser Gly Thr Asp Tyr Ser Phe Thr Ile Ser Ser Leu Glu Pro
65                  70                  75                  80
```

Glu Asp Val Ala Ser Tyr Phe Cys Gln His Tyr Phe His Tyr Pro Arg
85 90 95

Thr Phe Gly Ala Gly Thr Lys Val Glu Leu Lys
100 105

<210> SEQ ID NO 14
<211> LENGTH: 107
<212> TYPE: PRT
<213> ORGANISM: Artificial Sequence
<220> FEATURE:
<223> OTHER INFORMATION: Caninized anti-NGF

<400> SEQUENCE: 14

Glu Ile Val Met Thr Gln Ser Pro Ala Ser Leu Ser Leu Ser Gln Glu
1 5 10 15

Glu Lys Val Thr Ile Thr Cys Arg Ala Ser Glu Asp Ile Tyr Asn Ala
20 25 30

Leu Ala Trp Tyr Gln Gln Lys Pro Gly Gln Ala Pro Lys Leu Leu Ile
35 40 45

Tyr Asn Thr Asp Thr Leu His Thr Gly Val Pro Ser Arg Phe Ser Gly
50 55 60

Ser Gly Ser Gly Thr Asp Tyr Ser Phe Thr Ile Ser Ser Leu Glu Pro
65 70 75 80

Glu Asp Val Ala Ser Tyr Phe Cys Gln His Tyr Phe His Tyr Pro Arg
85 90 95

Thr Phe Gly Ala Gly Thr Lys Val Glu Leu Lys
100 105

<210> SEQ ID NO 15
<211> LENGTH: 107
<212> TYPE: PRT
<213> ORGANISM: Artificial Sequence
<220> FEATURE:
<223> OTHER INFORMATION: Caninized anti-NGF

<400> SEQUENCE: 15

Glu Ile Val Met Thr Gln Ser Pro Ala Ser Leu Ser Leu Ser Gln Glu
1 5 10 15

Glu Lys Val Thr Ile Thr Cys Arg Ala Ser Glu Asp Ile Tyr Asn Ala
20 25 30

Leu Ala Trp Tyr Gln Gln Lys Pro Gly Gln Ala Pro Lys Leu Leu Ile
35 40 45

Tyr Asn Thr Asp Thr Leu His Thr Gly Val Pro Ser Arg Phe Ser Gly
50 55 60

Ser Gly Ser Gly Thr Asp Tyr Ser Phe Thr Ile Ser Ser Leu Glu Pro
65 70 75 80

Glu Asp Val Ala Val Tyr Phe Cys Gln His Tyr Phe His Tyr Pro Arg
85 90 95

Thr Phe Gly Ala Gly Thr Lys Val Glu Leu Lys
100 105

<210> SEQ ID NO 16
<211> LENGTH: 25
<212> TYPE: PRT
<213> ORGANISM: canis familiaris

<400> SEQUENCE: 16

Gln Val Gln Leu Gln Glu Ser Gly Pro Gly Leu Val Lys Pro Ser Gln
1 5 10 15

Thr Leu Ser Leu Thr Cys Thr Val Ser
20 25

<210> SEQ ID NO 17
<211> LENGTH: 14
<212> TYPE: PRT
<213> ORGANISM: canis familiaris

<400> SEQUENCE: 17

Trp Val Arg Gln Arg Thr Gly Arg Gly Leu Glu Trp Met Gly
1 5 10

<210> SEQ ID NO 18
<211> LENGTH: 32
<212> TYPE: PRT
<213> ORGANISM: canis familiaris

<400> SEQUENCE: 18

Arg Leu Ser Ile Thr Arg Asp Thr Ala Lys Ser Gln Val Ser Leu Gln
1 5 10 15

Met Ser Ser Met Thr Thr Glu Asp Thr Ala Thr Tyr Tyr Cys Ala Arg
20 25 30

<210> SEQ ID NO 19
<211> LENGTH: 11
<212> TYPE: PRT
<213> ORGANISM: canis familiaris

<400> SEQUENCE: 19

Trp Gly Gln Gly Thr Ser Val Thr Val Ser Ser
1 5 10

<210> SEQ ID NO 20
<211> LENGTH: 25
<212> TYPE: PRT
<213> ORGANISM: canis familiaris

<400> SEQUENCE: 20

Gln Val Gln Leu Gln Glu Ser Gly Pro Gly Leu Val Lys Pro Ser Gln
1 5 10 15

Thr Leu Ser Leu Thr Cys Thr Val Ser
20 25

<210> SEQ ID NO 21
<211> LENGTH: 14
<212> TYPE: PRT
<213> ORGANISM: canis familiaris

<400> SEQUENCE: 21

Trp Val Arg Gln Arg Pro Gly Arg Gly Leu Glu Trp Met Gly
1 5 10

<210> SEQ ID NO 22
<211> LENGTH: 32
<212> TYPE: PRT
<213> ORGANISM: canis familiaris

<400> SEQUENCE: 22

Arg Leu Ser Ile Thr Arg Asp Thr Ala Lys Ser Gln Val Ser Leu Gln
1 5 10 15

Met Ser Ser Met Thr Thr Glu Asp Thr Ala Thr Tyr Tyr Cys Ala Arg
20 25 30

<210> SEQ ID NO 23
<211> LENGTH: 11
<212> TYPE: PRT
<213> ORGANISM: canis familiaris

<400> SEQUENCE: 23

Trp Gly Gln Gly Thr Leu Val Thr Val Ser Ser
1 5 10

<210> SEQ ID NO 24
<211> LENGTH: 25
<212> TYPE: PRT
<213> ORGANISM: canis familiaris

<400> SEQUENCE: 24

Gln Val Gln Leu Gln Glu Ser Gly Pro Gly Leu Val Lys Pro Ser Gln
1 5 10 15

Thr Leu Ser Leu Thr Cys Thr Val Ser
20 25

<210> SEQ ID NO 25
<211> LENGTH: 14
<212> TYPE: PRT
<213> ORGANISM: canis familiaris

<400> SEQUENCE: 25

Trp Val Arg Gln Arg Pro Gly Arg Gly Leu Glu Trp Met Gly
1 5 10

<210> SEQ ID NO 26
<211> LENGTH: 32
<212> TYPE: PRT
<213> ORGANISM: canis familiaris

<400> SEQUENCE: 26

Arg Ile Ser Ile Thr Arg Asp Thr Ala Lys Ser Gln Val Ser Leu Gln
1 5 10 15

Leu Ser Ser Met Thr Thr Glu Asp Thr Ala Thr Tyr Tyr Cys Ala Arg
20 25 30

<210> SEQ ID NO 27
<211> LENGTH: 11
<212> TYPE: PRT
<213> ORGANISM: canis familiaris

<400> SEQUENCE: 27

Trp Gly Gln Gly Thr Leu Val Thr Val Ser Ser
1 5 10

<210> SEQ ID NO 28
<211> LENGTH: 25
<212> TYPE: PRT
<213> ORGANISM: canis familiaris

<400> SEQUENCE: 28

Glu Val Thr Leu Gln Glu Ser Gly Pro Gly Leu Val Lys Pro Ser Gln
1 5 10 15

Thr Leu Ser Leu Thr Cys Thr Val Ser
20 25

<210> SEQ ID NO 29
<211> LENGTH: 14
<212> TYPE: PRT

<213> ORGANISM: canis familiaris

<400> SEQUENCE: 29

Trp Val Arg Gln Arg Pro Gly Arg Gly Leu Glu Trp Met Gly
1 5 10

<210> SEQ ID NO 30
<211> LENGTH: 32
<212> TYPE: PRT
<213> ORGANISM: canis familiaris

<400> SEQUENCE: 30

Arg Ile Ser Ile Thr Arg Asp Thr Ala Lys Asn Gln Val Ser Leu Gln
1 5 10 15

Leu Ser Ser Met Thr Thr Glu Asp Thr Ala Thr Tyr Tyr Cys Ala Arg
20 25 30

<210> SEQ ID NO 31
<211> LENGTH: 11
<212> TYPE: PRT
<213> ORGANISM: canis familiaris

<400> SEQUENCE: 31

Trp Gly Gln Gly Thr Leu Val Thr Val Ser Ser
1 5 10

<210> SEQ ID NO 32
<211> LENGTH: 25
<212> TYPE: PRT
<213> ORGANISM: canis familiaris

<400> SEQUENCE: 32

Glu Val Thr Leu Gln Glu Ser Gly Pro Gly Leu Val Lys Pro Ser Gln
1 5 10 15

Thr Leu Ser Leu Thr Cys Val Val Ser
20 25

<210> SEQ ID NO 33
<211> LENGTH: 14
<212> TYPE: PRT
<213> ORGANISM: canis familiaris

<400> SEQUENCE: 33

Trp Val Arg Gln Arg Pro Gly Arg Gly Leu Glu Trp Met Gly
1 5 10

<210> SEQ ID NO 34
<211> LENGTH: 32
<212> TYPE: PRT
<213> ORGANISM: canis familiaris

<400> SEQUENCE: 34

Arg Ile Ser Ile Thr Arg Asp Thr Ala Lys Asn Gln Val Ser Leu Gln
1 5 10 15

Leu Ser Ser Met Thr Thr Glu Asp Thr Ala Val Tyr Tyr Cys Ala Arg
20 25 30

<210> SEQ ID NO 35
<211> LENGTH: 11
<212> TYPE: PRT
<213> ORGANISM: canis familiaris

<400> SEQUENCE: 35

Trp Gly Gln Gly Thr Leu Val Thr Val Ser Ser
1               5                   10

<210> SEQ ID NO 36
<211> LENGTH: 23
<212> TYPE: PRT
<213> ORGANISM: canis familiaris

<400> SEQUENCE: 36

Asp Ile Gln Met Thr Gln Ser Pro Ala Ser Leu Ser Leu Ser Gln Glu
1               5                   10                  15

Glu Lys Val Thr Ile Thr Cys
            20

<210> SEQ ID NO 37
<211> LENGTH: 15
<212> TYPE: PRT
<213> ORGANISM: canis familiaris

<400> SEQUENCE: 37

Trp Tyr Gln Gln Lys Pro Gly Gln Ala Pro Lys Leu Leu Ile Tyr
1               5                   10                  15

<210> SEQ ID NO 38
<211> LENGTH: 32
<212> TYPE: PRT
<213> ORGANISM: canis familiaris

<400> SEQUENCE: 38

Gly Val Pro Ser Arg Phe Ser Gly Ser Gly Ser Gly Thr Asp Tyr Ser
1               5                   10                  15

Phe Thr Ile Ser Ser Leu Glu Ser Glu Asp Val Ala Ser Tyr Phe Cys
            20                  25                  30

<210> SEQ ID NO 39
<211> LENGTH: 10
<212> TYPE: PRT
<213> ORGANISM: canis familiaris

<400> SEQUENCE: 39

Phe Gly Ala Gly Thr Lys Val Glu Leu Lys
1               5                   10

<210> SEQ ID NO 40
<211> LENGTH: 23
<212> TYPE: PRT
<213> ORGANISM: canis familiaris

<400> SEQUENCE: 40

Asp Ile Gln Met Thr Gln Ser Pro Ala Ser Leu Ser Leu Ser Gln Glu
1               5                   10                  15

Glu Lys Val Thr Ile Thr Cys
            20

<210> SEQ ID NO 41
<211> LENGTH: 15
<212> TYPE: PRT
<213> ORGANISM: canis familiaris

<400> SEQUENCE: 41

Trp Tyr Gln Gln Lys Pro Gly Gln Ala Pro Lys Leu Leu Ile Tyr
1 5 10 15

<210> SEQ ID NO 42
<211> LENGTH: 32
<212> TYPE: PRT
<213> ORGANISM: canis familiaris

<400> SEQUENCE: 42

Gly Val Pro Ser Arg Phe Ser Gly Ser Gly Ser Gly Thr Asp Tyr Ser
1 5 10 15

Phe Thr Ile Ser Ser Leu Glu Pro Glu Asp Val Ala Ser Tyr Phe Cys
20 25 30

<210> SEQ ID NO 43
<211> LENGTH: 10
<212> TYPE: PRT
<213> ORGANISM: canis familiaris

<400> SEQUENCE: 43

Phe Gly Ala Gly Thr Lys Val Glu Leu Lys
1 5 10

<210> SEQ ID NO 44
<211> LENGTH: 23
<212> TYPE: PRT
<213> ORGANISM: canis familiaris

<400> SEQUENCE: 44

Glu Ile Val Met Thr Gln Ser Pro Ala Ser Leu Ser Leu Ser Gln Glu
1 5 10 15

Glu Lys Val Thr Ile Thr Cys
20

<210> SEQ ID NO 45
<211> LENGTH: 15
<212> TYPE: PRT
<213> ORGANISM: canis familiaris

<400> SEQUENCE: 45

Trp Tyr Gln Gln Lys Pro Gly Gln Ala Pro Lys Leu Leu Ile Tyr
1 5 10 15

<210> SEQ ID NO 46
<211> LENGTH: 32
<212> TYPE: PRT
<213> ORGANISM: canis familiaris

<400> SEQUENCE: 46

Gly Val Pro Ser Arg Phe Ser Gly Ser Gly Ser Gly Thr Asp Tyr Ser
1 5 10 15

Phe Thr Ile Ser Ser Leu Glu Pro Glu Asp Val Ala Ser Tyr Phe Cys
20 25 30

<210> SEQ ID NO 47
<211> LENGTH: 10
<212> TYPE: PRT
<213> ORGANISM: canis familiaris

<400> SEQUENCE: 47

Phe Gly Ala Gly Thr Lys Val Glu Leu Lys
1 5 10

<210> SEQ ID NO 48
<211> LENGTH: 23
<212> TYPE: PRT
<213> ORGANISM: canis familiaris

<400> SEQUENCE: 48

Glu Ile Val Met Thr Gln Ser Pro Ala Ser Leu Ser Leu Ser Gln Glu
1 5 10 15

Glu Lys Val Thr Ile Thr Cys
20

<210> SEQ ID NO 49
<211> LENGTH: 15
<212> TYPE: PRT
<213> ORGANISM: canis familiaris

<400> SEQUENCE: 49

Trp Tyr Gln Gln Lys Pro Gly Gln Ala Pro Lys Leu Leu Ile Tyr
1 5 10 15

<210> SEQ ID NO 50
<211> LENGTH: 32
<212> TYPE: PRT
<213> ORGANISM: canis familiaris

<400> SEQUENCE: 50

Gly Val Pro Ser Arg Phe Ser Gly Ser Gly Ser Gly Thr Asp Tyr Ser
1 5 10 15

Phe Thr Ile Ser Ser Leu Glu Pro Glu Asp Val Ala Val Tyr Phe Cys
20 25 30

<210> SEQ ID NO 51
<211> LENGTH: 10
<212> TYPE: PRT
<213> ORGANISM: canis familiaris

<400> SEQUENCE: 51

Phe Gly Ala Gly Thr Lys Val Glu Leu Lys
1 5 10

<210> SEQ ID NO 52
<211> LENGTH: 122
<212> TYPE: PRT
<213> ORGANISM: Artificial Sequence
<220> FEATURE:
<223> OTHER INFORMATION: Felinized anti-NGF antibody, Fe1

<400> SEQUENCE: 52

Gln Val Gln Leu Met Glu Ser Gly Ala Asp Leu Val Gln Pro Ser Glu
1 5 10 15

Ser Leu Arg Leu Thr Cys Val Ala Ser Gly Leu Ser Leu Thr Asn Asn
20 25 30

Asn Val Asn Trp Val Arg Gln Ala Pro Gly Lys Gly Leu Glu Trp Met
35 40 45

Gly Gly Val Trp Ala Gly Gly Ala Thr Asp Tyr Asn Ser Ala Leu Lys
50 55 60

Ser Arg Leu Thr Ile Thr Arg Asp Thr Ser Lys Asn Thr Val Phe Leu
65 70 75 80

Gln Met His Ser Leu Gln Ser Glu Asp Thr Ala Thr Tyr Tyr Cys Ala
85 90 95

Arg Asp Gly Gly Tyr Ser Ser Ser Thr Leu Tyr Ala Met Asp Ala Trp
100 105 110

Gly Gln Gly Thr Thr Val Thr Val Ser Ala
115 120

<210> SEQ ID NO 53
<211> LENGTH: 107
<212> TYPE: PRT
<213> ORGANISM: Artificial Sequence
<220> FEATURE:
<223> OTHER INFORMATION: Felinized anti-NGF antibody, Fe1

<400> SEQUENCE: 53

Asp Ile Glu Met Thr Gln Ser Pro Leu Ser Leu Ser Ala Thr Pro Gly
1 5 10 15

Glu Thr Val Ser Ile Ser Cys Arg Ala Ser Glu Asp Ile Tyr Asn Ala
20 25 30

Leu Ala Trp Tyr Leu Gln Lys Pro Gly Arg Ser Pro Arg Leu Leu Ile
35 40 45

Tyr Asn Thr Asp Thr Leu His Thr Gly Val Pro Asp Arg Phe Ser Gly
50 55 60

Ser Gly Ser Gly Thr Asp Phe Thr Leu Lys Ile Ser Arg Val Gln Thr
65 70 75 80

Glu Asp Val Gly Val Tyr Phe Cys Gln His Tyr Phe His Tyr Pro Arg
85 90 95

Thr Phe Gly Gln Gly Thr Lys Leu Glu Leu Lys
100 105

<210> SEQ ID NO 54
<211> LENGTH: 25
<212> TYPE: PRT
<213> ORGANISM: Felis catus

<400> SEQUENCE: 54

Gln Val Gln Leu Met Glu Ser Gly Ala Asp Leu Val Gln Pro Ser Glu
1 5 10 15

Ser Leu Arg Leu Thr Cys Val Ala Ser
20 25

<210> SEQ ID NO 55
<211> LENGTH: 14
<212> TYPE: PRT
<213> ORGANISM: Felis catus

<400> SEQUENCE: 55

Trp Val Arg Gln Ala Pro Gly Lys Gly Leu Glu Trp Met Gly
1 5 10

<210> SEQ ID NO 56
<211> LENGTH: 32
<212> TYPE: PRT
<213> ORGANISM: Felis catus

<400> SEQUENCE: 56

Arg Leu Thr Ile Thr Arg Asp Thr Ser Lys Asn Thr Val Phe Leu Gln
1 5 10 15

```
Met His Ser Leu Gln Ser Glu Asp Thr Ala Thr Tyr Tyr Cys Ala Arg
            20                  25                  30


<210> SEQ ID NO 57
<211> LENGTH: 11
<212> TYPE: PRT
<213> ORGANISM: Felis catus

<400> SEQUENCE: 57

Trp Gly Gln Gly Thr Thr Val Thr Val Ser Ala
1               5                   10


<210> SEQ ID NO 58
<211> LENGTH: 23
<212> TYPE: PRT
<213> ORGANISM: Felis catus

<400> SEQUENCE: 58

Asp Ile Glu Met Thr Gln Ser Pro Leu Ser Leu Ser Ala Thr Pro Gly
1               5                   10                  15

Glu Thr Val Ser Ile Ser Cys
            20


<210> SEQ ID NO 59
<211> LENGTH: 15
<212> TYPE: PRT
<213> ORGANISM: Felis catus

<400> SEQUENCE: 59

Trp Tyr Leu Gln Lys Pro Gly Arg Ser Pro Arg Leu Leu Ile Tyr
1               5                   10                  15


<210> SEQ ID NO 60
<211> LENGTH: 32
<212> TYPE: PRT
<213> ORGANISM: Felis catus

<400> SEQUENCE: 60

Gly Val Pro Asp Arg Phe Ser Gly Ser Gly Ser Gly Thr Asp Phe Thr
1               5                   10                  15

Leu Lys Ile Ser Arg Val Gln Thr Glu Asp Val Gly Val Tyr Phe Cys
            20                  25                  30


<210> SEQ ID NO 61
<211> LENGTH: 10
<212> TYPE: PRT
<213> ORGANISM: Felis catus

<400> SEQUENCE: 61

Phe Gly Gln Gly Thr Lys Leu Glu Leu Lys
1               5                   10


<210> SEQ ID NO 62
<211> LENGTH: 476
<212> TYPE: PRT
<213> ORGANISM: Felis catus

<400> SEQUENCE: 62

Met Glu Trp Ser Trp Val Phe Leu Phe Phe Leu Ser Val Thr Thr Gly
1               5                   10                  15

Val His Ser Gln Val Gln Leu Met Glu Ser Gly Ala Asp Leu Val Gln
            20                  25                  30
```

```
Pro Ser Glu Ser Leu Arg Leu Thr Cys Val Ala Ser Gly Leu Ser Leu
        35                  40                  45

Thr Asn Asn Asn Val Asn Trp Val Arg Gln Ala Pro Gly Lys Gly Leu
    50                  55                  60

Glu Trp Met Gly Gly Val Trp Ala Gly Gly Ala Thr Asp Tyr Asn Ser
65                  70                  75                  80

Ala Leu Lys Ser Arg Leu Thr Ile Thr Arg Asp Thr Ser Lys Asn Thr
                85                  90                  95

Val Phe Leu Gln Met His Ser Leu Gln Ser Glu Asp Thr Ala Thr Tyr
            100                 105                 110

Tyr Cys Ala Arg Asp Gly Gly Tyr Ser Ser Ser Thr Leu Tyr Ala Met
        115                 120                 125

Asp Ala Trp Gly Gln Gly Thr Thr Val Thr Val Ser Ala Ala Ser Thr
    130                 135                 140

Thr Ala Pro Ser Val Phe Pro Leu Ala Pro Ser Cys Gly Thr Thr Ser
145                 150                 155                 160

Gly Ala Thr Val Ala Leu Ala Cys Leu Val Leu Gly Tyr Phe Pro Glu
                165                 170                 175

Pro Val Thr Val Ser Trp Asn Ser Gly Ala Leu Thr Ser Gly Val His
            180                 185                 190

Thr Phe Pro Ala Val Leu Gln Ala Ser Gly Leu Tyr Ser Leu Ser Ser
        195                 200                 205

Met Val Thr Val Pro Ser Ser Arg Trp Leu Ser Asp Thr Phe Thr Cys
    210                 215                 220

Asn Val Ala His Pro Pro Ser Asn Thr Lys Val Asp Lys Thr Val Arg
225                 230                 235                 240

Lys Thr Asp His Pro Pro Gly Pro Lys Pro Cys Asp Cys Pro Lys Cys
                245                 250                 255

Pro Pro Pro Glu Met Leu Gly Gly Pro Ser Ile Phe Ile Phe Pro Pro
            260                 265                 270

Lys Pro Lys Asp Thr Leu Ser Ile Ser Arg Thr Pro Glu Val Thr Cys
        275                 280                 285

Leu Val Val Asp Leu Gly Pro Asp Asp Ser Asp Val Gln Ile Thr Trp
    290                 295                 300

Phe Val Asp Asn Thr Gln Val Tyr Thr Ala Lys Thr Ser Pro Arg Glu
305                 310                 315                 320

Glu Gln Phe Asn Ser Thr Tyr Arg Val Val Ser Val Leu Pro Ile Leu
                325                 330                 335

His Gln Asp Trp Leu Lys Gly Lys Glu Phe Lys Cys Lys Val Asn Ser
            340                 345                 350

Lys Ser Leu Pro Ser Pro Ile Glu Arg Thr Ile Ser Lys Ala Lys Gly
        355                 360                 365

Gln Pro His Glu Pro Gln Val Tyr Val Leu Pro Pro Ala Gln Glu Glu
    370                 375                 380

Leu Ser Arg Asn Lys Val Ser Val Thr Cys Leu Ile Lys Ser Phe His
385                 390                 395                 400

Pro Pro Asp Ile Ala Val Glu Trp Glu Ile Thr Gly Gln Pro Glu Pro
                405                 410                 415

Glu Asn Asn Tyr Arg Thr Thr Pro Pro Gln Leu Asp Ser Asp Gly Thr
            420                 425                 430

Tyr Phe Val Tyr Ser Lys Leu Ser Val Asp Arg Ser His Trp Gln Arg
        435                 440                 445
```

Gly Asn Thr Tyr Thr Cys Ser Val Ser His Glu Ala Leu His Ser His
    450                 455                 460

His Thr Gln Lys Ser Leu Thr Gln Ser Pro Gly Lys
465                 470                 475

<210> SEQ ID NO 63
<211> LENGTH: 237
<212> TYPE: PRT
<213> ORGANISM: Felis catus

<400> SEQUENCE: 63

Met Ser Val Pro Thr Gln Val Leu Gly Leu Leu Leu Leu Trp Leu Thr
1               5                   10                  15

Asp Ala Arg Cys Asp Ile Glu Met Thr Gln Ser Pro Leu Ser Leu Ser
            20                  25                  30

Ala Thr Pro Gly Glu Thr Val Ser Ile Ser Cys Arg Ala Ser Glu Asp
        35                  40                  45

Ile Tyr Asn Ala Leu Ala Trp Tyr Leu Gln Lys Pro Gly Arg Ser Pro
    50                  55                  60

Arg Leu Leu Ile Tyr Asn Thr Asp Thr Leu His Thr Gly Val Pro Asp
65                  70                  75                  80

Arg Phe Ser Gly Ser Gly Ser Gly Thr Asp Phe Thr Leu Lys Ile Ser
                85                  90                  95

Arg Val Gln Thr Glu Asp Val Gly Val Tyr Phe Cys Gln His Tyr Phe
            100                 105                 110

His Tyr Pro Arg Thr Phe Gly Gln Gly Thr Lys Leu Glu Leu Lys Arg
        115                 120                 125

Ser Asp Ala Gln Pro Ser Val Phe Leu Phe Gln Pro Ser Leu Asp Glu
    130                 135                 140

Leu His Thr Gly Ser Ala Ser Ile Val Cys Ile Leu Asn Asp Phe Tyr
145                 150                 155                 160

Pro Lys Glu Val Asn Val Lys Trp Lys Val Asp Gly Val Val Gln Asn
                165                 170                 175

Lys Gly Ile Gln Glu Ser Thr Thr Glu Gln Asn Ser Lys Asp Ser Thr
            180                 185                 190

Tyr Ser Leu Ser Ser Thr Leu Thr Met Ser Ser Thr Glu Tyr Gln Ser
        195                 200                 205

His Glu Lys Phe Ser Cys Glu Val Thr His Lys Ser Leu Ala Ser Thr
    210                 215                 220

Leu Val Lys Ser Phe Asn Arg Ser Glu Cys Gln Arg Glu
225                 230                 235

<210> SEQ ID NO 64
<211> LENGTH: 1431
<212> TYPE: DNA
<213> ORGANISM: Felis catus

<400> SEQUENCE: 64
atggaatggt cctgggtgtt cctgttcttc ctgtctgtga ccaccggcgt gcactctcag 60
gtgcagttga tggaatctgg cgccgacctg gtgcagcctt ctgagtctct gagactgacc 120
tgtgtggcct ctggactgtc cctgaccaac aacaacgtga actgggtccg acaggctccc 180
ggcaaaggat tggaatggat gggcggagtt tgggctggcg gcgctaccga ttacaactct 240
gctctgaagt cccggctgac catcaccaga gacacctcca agaacaccgt gtttctgcag 300
atgcactccc tgcagtctga ggacaccgcc acctactact gtgctagaga tggcggctac 360

```
tccagcagca ccctgtacgc tatggatgct tggggccagg gcaccacagt gacagtgtct    420

gctgcttcta ccaccgctcc tagcgttttc cctctggctc cttcttgtgg caccacctct    480

ggtgctacag tggctctggc ttgtctggtg ctgggctact ttcctgagcc tgtgaccgtg    540

tcttggaact ccggtgctct gacatctggc gtgcacacct ttccagctgt gctgcaggct    600

tctggcctgt actctctgtc ctctatggtc accgtgcctt ccagcagatg gctgtccgac    660

accttcacct gtaacgtggc ccatcctcct agcaacacca aggtggacaa gaccgtgcgc    720

aagaccgatc atcctcctgg acctaagcct tgcgactgcc ctaagtgtcc tccacctgaa    780

atgctcggcg gaccctccat cttcatcttc ccacctaagc caaaggacac cctgtccatc    840

tctcggaccc ctgaagtcac ctgtctggtg gtggatctgg gccctgacga ctctgatgtg    900

cagatcactt ggtttgtgga caatacccag gtctacaccg ccaagacctc tccaagagag    960

gaacagttca actccaccta cagagtggtg tccgtgctgc ccatcctgca tcaggattgg   1020

ctgaagggca aagagttcaa gtgcaaagtg aactccaaga gcctgccttc tccaatcgag   1080

cggaccatct ctaaggctaa gggccagcct catgagcccc aggtttactc tccaatcgag   1140

cggaccatct ctaaggctaa gggccagcct catgagcccc aggtttacaa gagctttcac   1200

cctcctgata tcgccgtgga atgggagatc acaggccagc ctgagccaga gaacaactac   1260

agaaccacac ctcctcagct ggactccgac ggcacctact tcgtgtactc caagctgtcc   1320

gtggacagat cccactggca gagaggcaac acctatacct gctctgtgtc tcacgaggcc   1380

ctgcactccc atcacaccca gaagtctctg acccagtctc ctggcaagtg a            1431
```

<210> SEQ ID NO 65
<211> LENGTH: 712
<212> TYPE: DNA
<213> ORGANISM: Felis catus

<400> SEQUENCE: 65

```
atgtccgtgc ctacacaggt tctgggactg ctgctgctgt ggctgaccga cgctagatgc      60

gacatcgaga tgacccagtc tccactgagc ctgtctgcta cacctggcga gacagtgtcc     120

atctcctgca gagcctccga ggacatctac aacgccctgg cctggtatct gcagaagcct     180

ggcagatccc ctcggctgct gatctacaac accgatacac tgcacaccgg cgtgcccgac     240

agattttctg gctctggatc tggcaccgac ttcaccctga agatctccag agtgcagacc     300

gaggacgtgg gcgtgtactt ctgccagcac tactttcact accctcggac ctttggccag     360

ggcaccaagc tggaactgaa gagatctgac gcccagcctt ccgtgttcct gttccagcct     420

tctctggatg agctgcatac cggctctgcc tccatcgtgt gcatcctgaa cgacttctac     480

cccaaagaag tgaacgtgaa gtggaaggtg gacggcgtgg tgcagaacaa gggcatccaa     540

gagtctacca ccgagcagaa ctccaaggac tccacctaca gcctgagcag caccctgacc     600

atgtcctcca ccgagtacca gagccacgag aagttcagct gcgaagtgac ccacaagtcc     660

ctggcttcta ccctggtcaa gtccttcaac agatccgagt gccagcgcgt ga             712
```

<210> SEQ ID NO 66
<211> LENGTH: 10
<212> TYPE: PRT
<213> ORGANISM: Artificial Sequence
<220> FEATURE:
<223> OTHER INFORMATION: Felinized anti-NGF antibody

<400> SEQUENCE: 66

Gly Leu Ser Leu Thr Asn Asn Asn Val Asn
1 5 10

<210> SEQ ID NO 67
<211> LENGTH: 16
<212> TYPE: PRT
<213> ORGANISM: Artificial Sequence
<220> FEATURE:
<223> OTHER INFORMATION: Felinized anti-NGF antibody

<400> SEQUENCE: 67

Gly Val Trp Ala Gly Gly Ala Thr Asp Tyr Asn Ser Ala Leu Lys Ser
1 5 10 15

<210> SEQ ID NO 68
<211> LENGTH: 14
<212> TYPE: PRT
<213> ORGANISM: Artificial Sequence
<220> FEATURE:
<223> OTHER INFORMATION: Felinized anti-NGF antibody

<400> SEQUENCE: 68

Asp Gly Gly Tyr Ser Ser Ser Thr Leu Tyr Ala Met Asp Ala
1 5 10

<210> SEQ ID NO 69
<211> LENGTH: 10
<212> TYPE: PRT
<213> ORGANISM: Artificial Sequence
<220> FEATURE:
<223> OTHER INFORMATION: Felinized anti-NGF antibody variant

<400> SEQUENCE: 69

Gly Phe Ser Leu Thr Asn Asn Asn Val Asn
1 5 10

<210> SEQ ID NO 70
<211> LENGTH: 16
<212> TYPE: PRT
<213> ORGANISM: Artificial Sequence
<220> FEATURE:
<223> OTHER INFORMATION: Felinized anti-NGF antibody variant

<400> SEQUENCE: 70

Gly Val Trp Ala Gly Gly Ala Thr Asp Tyr Asn Ser Ala Val Lys Ser
1 5 10 15

<210> SEQ ID NO 71
<211> LENGTH: 14
<212> TYPE: PRT
<213> ORGANISM: Artificial Sequence
<220> FEATURE:
<223> OTHER INFORMATION: Felinized anti-NGF antibody variant

<400> SEQUENCE: 71

Asp Gly Gly Tyr Ser Ser Ser Thr Leu Tyr Ala Met Asp Ala
1 5 10

<210> SEQ ID NO 72
<211> LENGTH: 10
<212> TYPE: PRT
<213> ORGANISM: Artificial Sequence
<220> FEATURE:
<223> OTHER INFORMATION: Felinized anti-NGF antibody variant

<400> SEQUENCE: 72

Gly Phe Ser Leu Thr Asn Asn Asn Val Asn
1 5 10

<210> SEQ ID NO 73
<211> LENGTH: 16
<212> TYPE: PRT
<213> ORGANISM: Artificial Sequence
<220> FEATURE:
<223> OTHER INFORMATION: Felinized anti-NGF antibody variant

<400> SEQUENCE: 73

Gly Val Trp Ala Gly Gly Ala Thr Asp Tyr Asn Ser Ala Leu Lys Ser
1 5 10 15

<210> SEQ ID NO 74
<211> LENGTH: 14
<212> TYPE: PRT
<213> ORGANISM: Artificial Sequence
<220> FEATURE:
<223> OTHER INFORMATION: Felinized anti-NGF antibody variant

<400> SEQUENCE: 74

Asp Gly Gly Tyr Ser Ser Ser Thr Leu Tyr Ala Met Asp Val
1 5 10

<210> SEQ ID NO 75
<211> LENGTH: 10
<212> TYPE: PRT
<213> ORGANISM: Artificial Sequence
<220> FEATURE:
<223> OTHER INFORMATION: Felinized anti-NGF antibody variant

<400> SEQUENCE: 75

Gly Phe Ser Leu Thr Asn Asn Asn Val Asn
1 5 10

<210> SEQ ID NO 76
<211> LENGTH: 16
<212> TYPE: PRT
<213> ORGANISM: Artificial Sequence
<220> FEATURE:
<223> OTHER INFORMATION: Felinized anti-NGF antibody variant

<400> SEQUENCE: 76

Gly Val Trp Ala Gly Gly Ala Thr Asp Tyr Asn Ser Ala Leu Lys Ser
1 5 10 15

<210> SEQ ID NO 77
<211> LENGTH: 14
<212> TYPE: PRT
<213> ORGANISM: Artificial Sequence
<220> FEATURE:
<223> OTHER INFORMATION: Felinized anti-NGF antibody variant

<400> SEQUENCE: 77

Asp Gly Gly Tyr Ser Ser Ser Thr Leu Tyr Ala Met Glu Ala
1 5 10

<210> SEQ ID NO 78
<211> LENGTH: 10
<212> TYPE: PRT
<213> ORGANISM: rat rattus

<400> SEQUENCE: 78

Gly Phe Ser Leu Thr Asn Asn Asn Val Asn
1 5 10

<210> SEQ ID NO 79
<211> LENGTH: 16
<212> TYPE: PRT
<213> ORGANISM: rat rattus

<400> SEQUENCE: 79

Gly Val Trp Ala Gly Gly Ala Thr Asp Tyr Asn Ser Ala Leu Lys Ser
1 5 10 15

<210> SEQ ID NO 80
<211> LENGTH: 14
<212> TYPE: PRT
<213> ORGANISM: rat rattus

<400> SEQUENCE: 80

Asp Gly Gly Tyr Ser Ser Ser Thr Leu Tyr Ala Met Asp Ala
1 5 10

<210> SEQ ID NO 81
<211> LENGTH: 10
<212> TYPE: PRT
<213> ORGANISM: Artificial Sequence
<220> FEATURE:
<223> OTHER INFORMATION: Caninized anti-NGF antibody variant

<400> SEQUENCE: 81

Gly Leu Ser Leu Thr Asn Asn Asn Val Asn
1 5 10

<210> SEQ ID NO 82
<211> LENGTH: 16
<212> TYPE: PRT
<213> ORGANISM: Artificial Sequence
<220> FEATURE:
<223> OTHER INFORMATION: Caninized anti-NGF antibody variant

<400> SEQUENCE: 82

Gly Val Trp Ala Gly Gly Ala Thr Asp Tyr Asn Ser Ala Leu Lys Ser
1 5 10 15

<210> SEQ ID NO 83
<211> LENGTH: 14
<212> TYPE: PRT
<213> ORGANISM: Artificial Sequence
<220> FEATURE:
<223> OTHER INFORMATION: Caninized anti-NGF antibody variant

<400> SEQUENCE: 83

Asp Gly Gly Tyr Ser Ser Ser Thr Leu Tyr Ala Met Asp Ala
1 5 10

<210> SEQ ID NO 84
<211> LENGTH: 10
<212> TYPE: PRT
<213> ORGANISM: Artificial Sequence
<220> FEATURE:
<223> OTHER INFORMATION: Caninized anti-NGF antibody variant

<400> SEQUENCE: 84

Gly Phe Ser Leu Thr Asn Asn Asn Val Asn
1 5 10

<210> SEQ ID NO 85
<211> LENGTH: 16
<212> TYPE: PRT
<213> ORGANISM: Artificial Sequence
<220> FEATURE:
<223> OTHER INFORMATION: Caninized anti-NGF antibody variant

<400> SEQUENCE: 85

Gly Val Trp Ala Gly Gly Ala Thr Asp Tyr Asn Ser Ala Val Lys Ser
1 5 10 15

<210> SEQ ID NO 86
<211> LENGTH: 14
<212> TYPE: PRT
<213> ORGANISM: Artificial Sequence
<220> FEATURE:
<223> OTHER INFORMATION: Caninized anti-NGF antibody variant

<400> SEQUENCE: 86

Asp Gly Gly Tyr Ser Ser Ser Thr Leu Tyr Ala Met Asp Ala
1 5 10

<210> SEQ ID NO 87
<211> LENGTH: 10
<212> TYPE: PRT
<213> ORGANISM: Artificial Sequence
<220> FEATURE:
<223> OTHER INFORMATION: Caninized anti-NGF antibody variant

<400> SEQUENCE: 87

Gly Phe Ser Leu Thr Asn Asn Asn Val Asn
1 5 10

<210> SEQ ID NO 88
<211> LENGTH: 16
<212> TYPE: PRT
<213> ORGANISM: Artificial Sequence
<220> FEATURE:
<223> OTHER INFORMATION: Caninized anti-NGF antibody variant

<400> SEQUENCE: 88

Gly Val Trp Ala Gly Gly Ala Thr Asp Tyr Asn Ser Ala Leu Lys Ser
1 5 10 15

<210> SEQ ID NO 89
<211> LENGTH: 14
<212> TYPE: PRT
<213> ORGANISM: Artificial Sequence
<220> FEATURE:
<223> OTHER INFORMATION: Caninized anti-NGF antibody variant

<400> SEQUENCE: 89

Asp Gly Gly Tyr Ser Ser Ser Thr Leu Tyr Ala Met Asp Val
1 5 10

<210> SEQ ID NO 90
<211> LENGTH: 10
<212> TYPE: PRT
<213> ORGANISM: Artificial Sequence
<220> FEATURE:
<223> OTHER INFORMATION: Caninized anti-NGF antibody variant

<400> SEQUENCE: 90

Gly Phe Ser Leu Thr Asn Asn Asn Val Asn
1 5 10

```
<210> SEQ ID NO 91
<211> LENGTH: 16
<212> TYPE: PRT
<213> ORGANISM: Artificial Sequence
<220> FEATURE:
<223> OTHER INFORMATION: Caninized anti-NGF antibody variant

<400> SEQUENCE: 91

Gly Val Trp Ala Gly Gly Ala Thr Asp Tyr Asn Ser Ala Leu Lys Ser
1               5                   10                  15


<210> SEQ ID NO 92
<211> LENGTH: 14
<212> TYPE: PRT
<213> ORGANISM: Artificial Sequence
<220> FEATURE:
<223> OTHER INFORMATION: Caninized anti-NGF antibody variant

<400> SEQUENCE: 92

Asp Gly Gly Tyr Ser Ser Ser Thr Leu Tyr Ala Met Glu Ala
1               5                   10


<210> SEQ ID NO 93
<211> LENGTH: 10
<212> TYPE: PRT
<213> ORGANISM: Artificial Sequence
<220> FEATURE:
<223> OTHER INFORMATION: Caninized anti-NGF antibody variant

<400> SEQUENCE: 93

Thr Leu Ser Leu Thr Asn Asn Asn Val Asn
1               5                   10


<210> SEQ ID NO 94
<211> LENGTH: 10
<212> TYPE: PRT
<213> ORGANISM: Artificial Sequence
<220> FEATURE:
<223> OTHER INFORMATION: Caninized anti-NGF antibody variant

<400> SEQUENCE: 94

Thr Phe Ser Leu Thr Asn Asn Asn Val Asn
1               5                   10


<210> SEQ ID NO 95
<211> LENGTH: 10
<212> TYPE: PRT
<213> ORGANISM: Artificial Sequence
<220> FEATURE:
<223> OTHER INFORMATION: Caninized anti-NGF antibody variant

<400> SEQUENCE: 95

Gly Leu Ser Leu Thr Asn Asn Asn Val Asn
1               5                   10
```